(12) United States Patent
Morales Delgado et al.

(10) Patent No.: US 11,622,686 B2
(45) Date of Patent: Apr. 11, 2023

(54) OPTICAL IMAGING WITH UNSHIFTED REFERENCE BEAM

(71) Applicant: Open Water Internet Inc., San Francisco, CA (US)

(72) Inventors: Edgar Emilio Morales Delgado, San Francisco, CA (US); Caitlin Regan, Sausalito, CA (US); Mary Lou Jepsen, Sausalito, CA (US); Hosain Haghany, San Francisco, CA (US); Sarmishtha Satpathy, San Francisco, CA (US); Wilson Toy, San Francisco, CA (US); Soren Konecky, Alameda, CA (US)

(73) Assignee: Open Water Internet, Inc., San Francisco, CA (US)

( * ) Notice: Subject to any disclaimer, the term of this patent is extended or adjusted under 35 U.S.C. 154(b) by 617 days.

(21) Appl. No.: 16/692,945

(22) Filed: Nov. 22, 2019

(65) Prior Publication Data

US 2021/0153743 A1 May 27, 2021

(51) Int. Cl.
| | |
|---|---|
| *G06T 5/50* | (2006.01) |
| *A61B 5/00* | (2006.01) |
| *H04N 5/33* | (2023.01) |
| *A61B 8/00* | (2006.01) |
| *G03H 1/04* | (2006.01) |

(52) U.S. Cl.
CPC ............ *A61B 5/0066* (2013.01); *A61B 8/00* (2013.01); *G03H 1/0443* (2013.01); *G06T 5/50* (2013.01); *H04N 5/33* (2013.01); *A61B 2562/0233* (2013.01); *A61B 2576/00* (2013.01); *G03H 2001/0452* (2013.01); *G03H 2222/16* (2013.01); *G06T 2207/10048* (2013.01); *G06T 2207/20212* (2013.01); *G06T 2207/30004* (2013.01)

(58) Field of Classification Search
CPC ........... A61B 5/0066; A61B 8/00; G06T 5/50; H04N 5/33; G03H 1/0443
See application file for complete search history.

(56) References Cited

U.S. PATENT DOCUMENTS

| | | | |
|---|---|---|---|
| 6,172,760 | B1 | 1/2001 | Son |
| 6,690,958 | B1 * | 2/2004 | Walker ................ A61B 8/4416 600/407 |
| 6,956,650 | B2 | 10/2005 | Boas |
| 7,119,906 | B2 | 10/2006 | Pepper |
| 7,460,248 | B2 | 12/2008 | Kurtz |
| 7,551,809 | B2 | 6/2009 | Taira |
| 7,610,082 | B2 | 10/2009 | Chance |

(Continued)

OTHER PUBLICATIONS

U.S. Appl. No. 16/692,898, unpublished, Morales Delgado.

(Continued)

*Primary Examiner* — Gregory M Desire
(74) *Attorney, Agent, or Firm* — Freestone Intellectual Property Law PLLC; Aaron J. Visbeek

(57) ABSTRACT

An ultrasound emitter launches an ultrasonic signal into a diffuse medium such as tissue. The diffuse medium is illuminated with an infrared illumination signal. activating an ultrasound emitter to launch an ultrasonic signal into a diffuse medium. An infrared reference beam is interfered with an infrared exit signal having an infrared wavelength that is the same as the infrared illumination signal. An infrared image is captured of the interference of the infrared reference beam with the infrared exit signal.

17 Claims, 14 Drawing Sheets

(56) References Cited

U.S. PATENT DOCUMENTS

| | | | |
|---|---|---|---|
| 7,647,091 | B2 | 1/2010 | Ntziachristos |
| 7,728,986 | B2 | 6/2010 | Lasker |
| 7,804,070 | B1 | 9/2010 | Pan |
| 7,821,640 | B2 | 10/2010 | Koenig |
| 7,822,468 | B2 | 10/2010 | Stammes |
| 7,826,878 | B2 | 11/2010 | Alfano |
| 7,898,649 | B2 | 3/2011 | Masumura |
| 7,965,389 | B2 | 6/2011 | Da Silva |
| 7,983,740 | B2 | 7/2011 | Culver |
| 7,928,896 | B2 | 8/2011 | Jin |
| 8,014,847 | B2 | 9/2011 | Shastri |
| 8,120,784 | B2 | 2/2012 | Da Silva |
| 8,170,651 | B2 | 5/2012 | Lorenzo |
| 8,239,006 | B2 | 8/2012 | Zhu |
| 8,263,947 | B2 | 9/2012 | Da Silva |
| 8,289,502 | B2 | 10/2012 | Koshida |
| 8,326,567 | B2 | 12/2012 | Masumura |
| 8,330,642 | B2 | 12/2012 | Jin |
| 8,355,131 | B2 | 1/2013 | Bakker |
| 8,357,915 | B2 | 1/2013 | Guyon |
| 8,374,409 | B2 | 2/2013 | Jochemsen |
| 8,416,421 | B2 | 4/2013 | Wang |
| 8,450,674 | B2 | 5/2013 | Yang |
| 8,451,450 | B2 | 5/2013 | Heng |
| 8,520,921 | B2 | 8/2013 | Ziegler |
| 8,525,998 | B2 | 9/2013 | Yaqoob |
| 8,527,242 | B2 | 9/2013 | Granot |
| 8,531,662 | B2 | 9/2013 | Van Der Mark |
| 8,563,932 | B2 | 10/2013 | Fang |
| 8,634,077 | B2 | 1/2014 | Hu |
| 8,649,015 | B2 | 2/2014 | Ichihara |
| 8,917,442 | B2 | 3/2014 | Baym |
| 8,717,574 | B2 | 5/2014 | Yang |
| 8,814,795 | B2 | 8/2014 | Derode |
| 8,817,255 | B2 | 8/2014 | Masumura |
| 8,830,573 | B2 | 9/2014 | Cui |
| 8,847,175 | B2 | 9/2014 | Laidevant |
| 8,937,284 | B2 | 1/2015 | Fang |
| 8,954,130 | B2 * | 2/2015 | Masumura ........... G01N 21/453 356/497 |
| 8,976,433 | B2 | 3/2015 | Masumura |
| 9,012,869 | B2 | 4/2015 | Andersson-Engels |
| 9,036,970 | B2 | 5/2015 | Guyon |
| 9,037,216 | B2 | 5/2015 | Hielscher |
| 9,057,695 | B2 | 6/2015 | Masumura |
| 9,131,851 | B2 | 9/2015 | Fukutani |
| 9,134,229 | B2 | 9/2015 | Lesage |
| 9,179,842 | B2 | 11/2015 | Nakaji |
| 9,207,171 | B2 | 12/2015 | Nadakuditi |
| 9,234,841 | B2 | 1/2016 | Wang |
| 9,282,932 | B2 | 3/2016 | Kudo |
| 9,297,752 | B2 | 3/2016 | Shimokawa |
| 9,304,490 | B2 | 4/2016 | Masumura |
| 9,313,423 | B2 | 4/2016 | Wang |
| 9,335,604 | B2 | 5/2016 | Popovich |
| 9,335,605 | B2 | 5/2016 | Wang |
| 9,341,569 | B2 | 5/2016 | 'T Hooft |
| 9,354,166 | B2 | 5/2016 | Judkewitz |
| 9,373,020 | B2 | 6/2016 | Kudo |
| 9,407,796 | B2 | 8/2016 | Dinten |
| 9,427,213 | B2 | 8/2016 | Suzuki |
| 9,480,425 | B2 | 11/2016 | Culver |
| 9,486,142 | B2 | 11/2016 | Hielscher |
| 9,488,574 | B2 | 11/2016 | Koehler |
| 9,509,956 | B2 | 11/2016 | Piestun |
| 9,622,663 | B2 | 4/2017 | Fang |
| 9,689,797 | B2 | 6/2017 | Sun |
| 9,724,489 | B2 | 8/2017 | Barbour |
| 9,730,649 | B1 | 8/2017 | Jepsen |
| 9,750,413 | B2 | 9/2017 | Sandusky |
| 9,906,870 | B2 * | 2/2018 | Shah ..................... H04R 1/42 |
| 9,931,040 | B2 * | 4/2018 | Homyk ............... A61B 5/0295 |
| 10,299,682 | B1 * | 5/2019 | Yang ................ A61B 5/14553 |
| 10,517,565 | B2 * | 12/2019 | Zhu ...................... A61B 8/5261 |
| 11,116,477 | B2 * | 9/2021 | Tokida ................ A61B 8/5223 |
| 11,357,407 | B2 * | 6/2022 | Someda ............... A61B 5/0095 |
| 2006/0106282 | A1 * | 5/2006 | Bala ..................... A61B 1/0638 600/181 |
| 2010/0016732 | A1 | 1/2010 | Wells |
| 2012/0070817 | A1 | 3/2012 | Wang et al. |
| 2014/0081096 | A1 | 3/2014 | Baym |
| 2014/0114181 | A1 | 4/2014 | Wu |
| 2014/0303473 | A1 | 10/2014 | Nanaumi |
| 2015/0182121 | A1 | 7/2015 | Barbour |
| 2015/0238092 | A1 | 8/2015 | Masumura |
| 2015/0241342 | A1 | 8/2015 | Zhou |
| 2015/0346027 | A1 | 12/2015 | Khare |
| 2015/0351635 | A1 | 12/2015 | Cerussi |
| 2016/0085135 | A1 | 3/2016 | Park |
| 2016/0157723 | A1 | 6/2016 | Kanick |
| 2016/0262723 | A1 | 9/2016 | Zhu |
| 2016/0363527 | A1 | 12/2016 | Ruan |
| 2017/0118423 | A1 | 4/2017 | Zhou |
| 2017/0163946 | A1 | 6/2017 | Komanduri |
| 2017/0168565 | A1 | 6/2017 | Cohen |
| 2017/0202633 | A1 | 7/2017 | Liu |
| 2017/0230555 | A1 | 8/2017 | Tabirian |
| 2017/0231501 | A1 | 8/2017 | Culver |
| 2021/0153743 | A1 * | 5/2021 | Morales Delgado ........ G03H 1/0443 |

OTHER PUBLICATIONS

Arridge et al. Nonuniqueness in diffusion-based optical tomography, Optics Letters, Jun. 1, 1998, vol. 23, No. 11, pp. 882-884.

Hofmann et al. Differential light detector, Rev. Sci. Instrum, Feb. 1979, vol. 50, No. 2, pp. 249-252.

Freund et al. Memory Effects in Propagation of Ooptical Waves through Disordered Media, Physical Review Letters, Nov. 14, 1988, vol. 61, No. 20, pp. 2328-2331.

Goodman et al. Wavefront-Reconstruction Imaging Through Random Media, Jun. 15, 1966, vol. 8, No. 12, pp. 311-313.

Peng et al. Low loss liquid crystals for infrared applications, Liquid Crystal, 2014, vol. 41, No. 11, pp. 1545-1552.

* cited by examiner

OPTICAL IMAGING WITH UNSHIFTED REFERENCE BEAM

CROSS REFERENCE TO RELATED APPLICATIONS

This application is related to U.S. non-provisional patent application entitled, "System for Optical Imaging with Unshifted Reference Beam," Ser. No. 16/692,898, filed the same day.

BACKGROUND INFORMATION

Imaging devices are used in contexts such as healthcare, navigation, and security, among others. Imaging systems often measure radio waves or light waves to facilitate imaging. Imaging that measures light scattered by an object is especially challenging and advances to the devices, systems, and methods to improve optical imaging are sought to increase speed, increase resolution, improve accuracy, reduce size and/or reduce cost.

BRIEF DESCRIPTION OF THE DRAWINGS

Non-limiting and non-exhaustive embodiments of the invention are described with reference to the following figures, wherein like reference numerals refer to like parts throughout the various views unless otherwise specified.

DETAILED DESCRIPTION

Figure 1A:
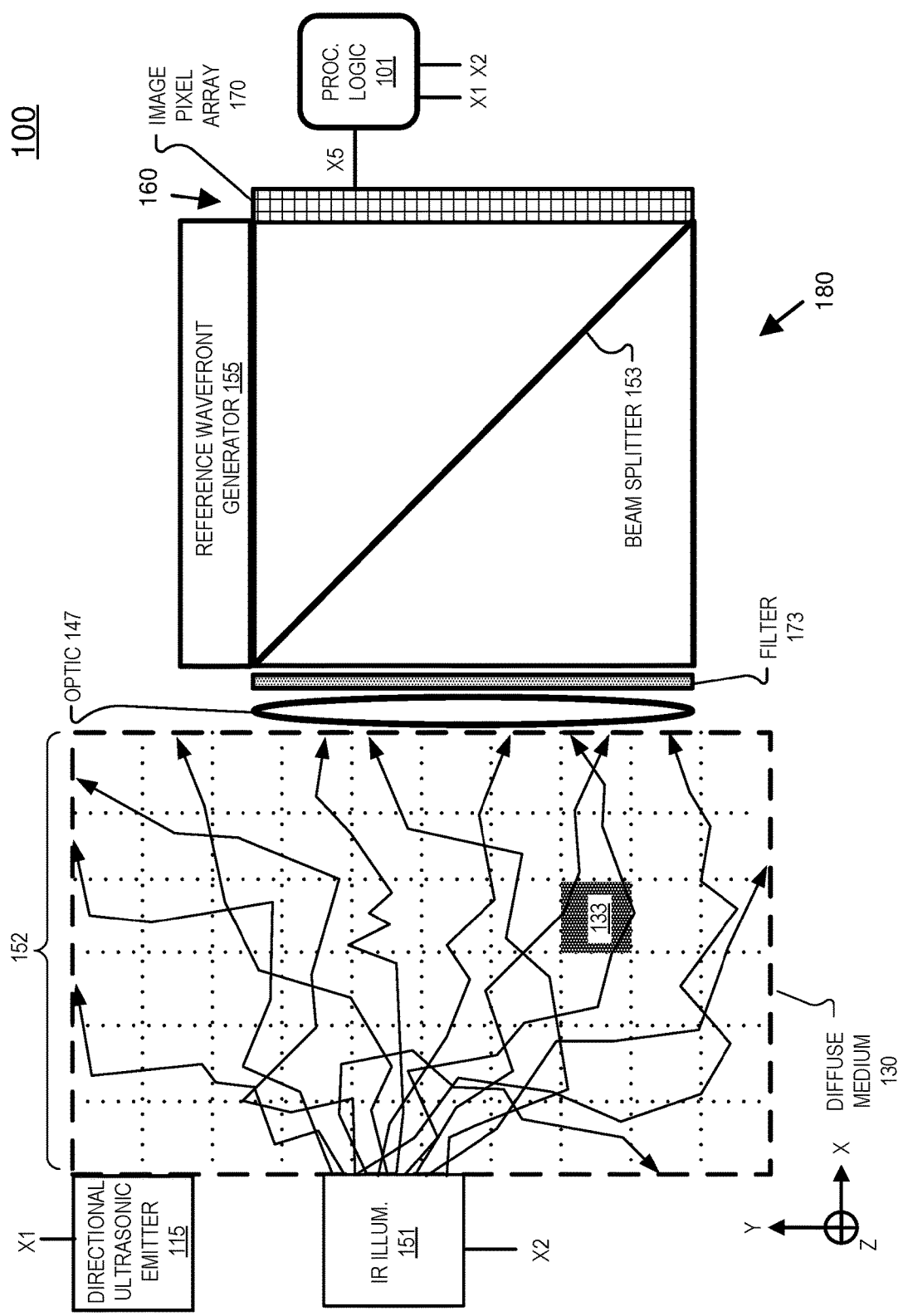
FIGS. 1A-1C illustrate an example imaging system that includes, an infrared illuminator, an image pixel array, and a beam splitter, in accordance with an embodiment of the disclosure.

Embodiments of a system, device, and method for optical imaging with an unshifted reference beam are described herein. In the following description, numerous specific details are set forth to provide a thorough understanding of the embodiments. One skilled in the relevant art will recognize, however, that the techniques described herein can be practiced without one or more of the specific details, or with other methods, components, materials, etc. In other instances, well-known structures, materials, or operations are not shown or described in detail to avoid obscuring certain aspects.

This disclosure will generally describe imaging a diffuse medium in the context of human tissue, however, the content of this disclosure may be applied to medical imaging, navigation, security, scientific research, or other contexts that image diffuse mediums or objects.

Human tissue is translucent to infrared light and to at least some wavelengths of visible light, although different parts of the human body (e.g. skin, blood, bone) exhibit different absorption coefficients. Researchers have attempted to use the properties of infrared light for medical imaging purposes, but size and cost constraints have been prohibitive for wide-scale adoption. Illuminating tissue and other diffuse mediums with visible light and near-infrared light for imaging purposes is sometimes referred to as Diffuse Optical Tomography. In one Diffuse Optical Tomography technique, time-of-flight (TOF) imaging can theoretically be employed by measuring the time it takes for "ballistic" photons (those photons that are not scattered) to pass through tissue. Since the ballistic photons reach the sensor the fastest, they are the least scattered (have the shortest optical path) and thus some conclusion can be drawn to create an image of the tissue that is illuminated by infrared light. However, TOF imaging generally requires specialty hardware (e.g. picosecond pulsed lasers and single photon detectors) to facilitate ultra-fast shutters on sensors that are able to image at the speed of light and the systems are overall very expensive and bulky. TOF imaging also requires an input of approximately 10-100 fold (or more) light intensity into the body than is received at the detector. Thus, efficacy and power limitations as well as safety limits on input intensity limit TOF imaging resolution, imaging depth and utility.

In contrast to TOF imaging, some embodiments of the disclosure may illuminate a diffuse medium (e.g. tissue) with an infrared illumination light. A base holographic infrared image of an interference of an infrared reference beam and an infrared exit signal may be captured while the infrared illumination light is illuminating the diffuse medium but an ultrasonic signal is not propagating through the diffuse medium. The base holographic infrared image may be captured by an image sensor, for example. The infrared exit signal is a portion of the infrared illumination light that exits the diffuse medium. The base holographic infrared image may therefore be used to establish a baseline quantity of light that exits the diffuse medium as the infrared exit signal while no ultrasonic signal is introduced to the diffuse medium. The infrared exit signal that exits the diffuse medium may be referred to as a base infrared exit signal when an ultrasonic signal is not propagating through the diffuse medium.

One or more additional holographic infrared images may be captured while an ultrasonic signal is directed to (or focused to) particular voxels. Those additional holographic images may be compared to the base holographic infrared image to generate a difference signal representative of a decrease in the infrared exit signal while the ultrasonic signal is directed to that particular voxel. The ultrasonic signal focused to the voxel will wavelength-shift a portion of the infrared illumination light that is propagating through the particular voxel to have an infrared wavelength that is slightly different than the narrow-band infrared wavelength of the infrared illumination light and the infrared reference beam. The wavelength-shifted light does not contribute to the interference with the infrared reference beam and thus the wavelength-shifted light represents a decrease in the infrared exit signal that interferes with the infrared reference beam and that decrease will be captured in the additional holographic images that are captured with the ultrasonic signals directed to particular voxels. The difference signals corresponding with different voxels can then be aggregated together into a composite image of the diffuse medium.

Applicant has utilized techniques that include directing an ultrasonic signal to a particular voxel and then capturing the interference of the wavelength-shifted portion of the infrared illumination light from that pixel. In other words, the amount of wavelength-shifted light for a particular voxel is measured. In that technique, the wavelength-shifted light and the infrared reference beam are the same wavelength, but the wavelength-shifted infrared light is a different wavelength than the infrared illumination light. In contrast to that technique, implementations of the disclosure include infrared illumination light that is a same infrared wavelength as the infrared reference beam and the infrared exit signal. And, the drop or absence of wavelength-shifted light for a particular voxel is measured with respect to a baseline measurement (e.g. a base holographic infrared image). These embodiments and others will be described in more detail with references to FIGS. 1A-8.

Reference throughout this specification to "one embodiment" or "an embodiment" means that a particular feature, structure, or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

Throughout this specification, several terms of art are used. These terms are to take on their ordinary meaning in the art from which they come, unless specifically defined herein or the context of their use would clearly suggest otherwise. For the purposes of the disclosure, visible light has a wavelength from approximately 400 nm to 700 nm and infrared light has a wavelength from approximately 700 nm to 1 mm. Near-infrared light has a wavelength from approximately 700 nm to 1400 nm.

Figure 1B:
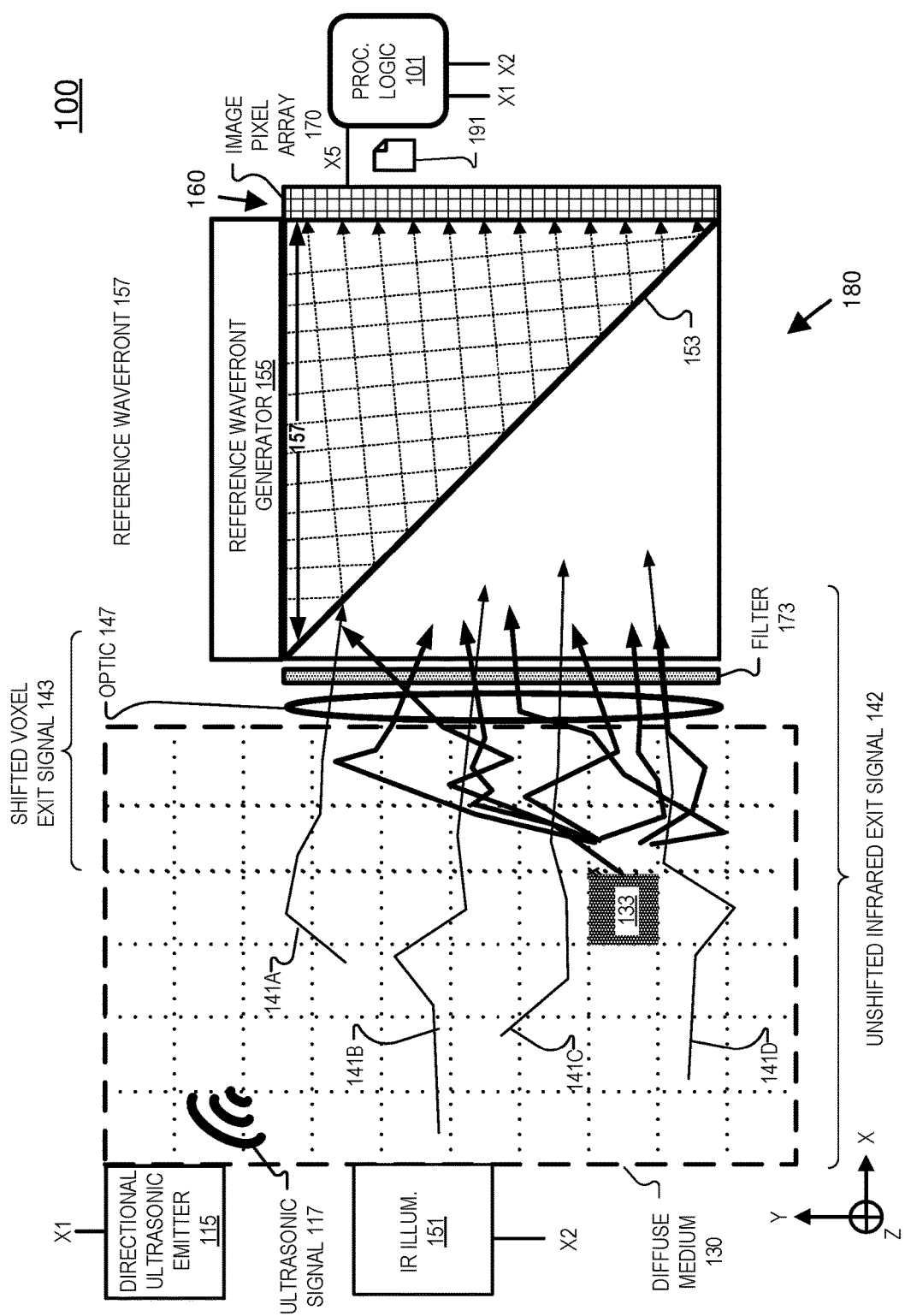
Figure 1C:
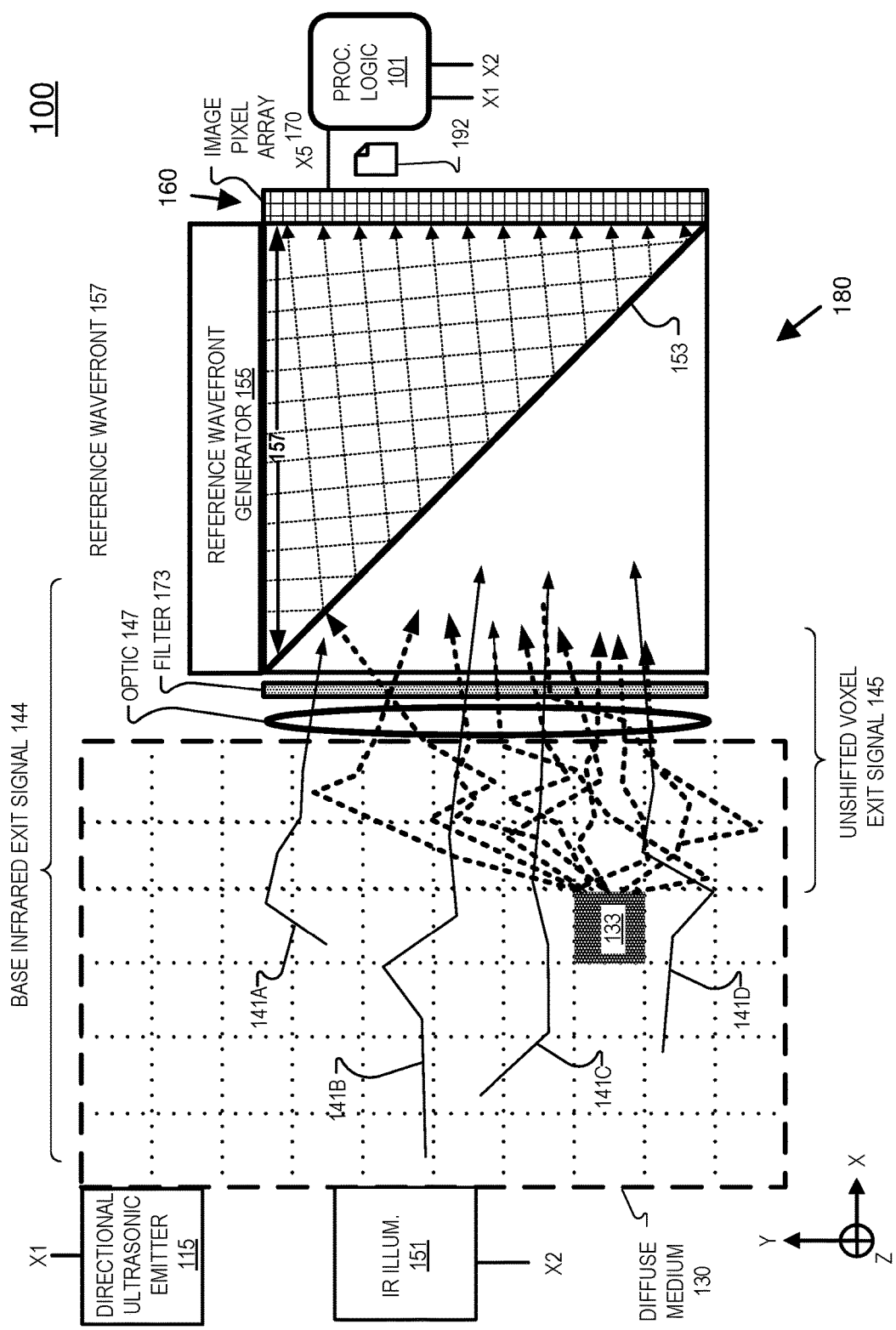

FIGS. 1A-1C illustrate an example imaging system that includes, an infrared illuminator, an image pixel array, and a beam splitter, in accordance with an embodiment of the disclosure. In FIG. 1A, imaging system 100 includes processing logic 101 and image module 160. Imaging module 160 includes image pixel array 170 and may include further optical components such as lenses or filters (not specifically illustrated). In FIG. 1A, imaging system 100 also includes a directional ultrasonic emitter 115 coupled to be driven by processing logic 101.

System 100 includes an infrared illuminator 151. Processing logic 101 is coupled to selectively activate infrared (IR) illuminator 151 via output X2, in the illustrated embodiment. Infrared illuminator 151 may include an infrared laser generating an infrared illumination signal 152. Of course, an infrared laser may generate monochromatic coherent infrared light. Monochromatic light may be defined as light within a 10 MHz frequency band, for example. In an embodiment, infrared illumination signal 152 has a linewidth of less than 11.5 fm. The infrared light that IR illuminator 151 emits may be centered around a frequency in the 680-1000 nm range while having a linewidth of less than 11.5 fm. In one embodiment, the infrared light that IR illuminator 151 emits may be centered around a frequency in the 1600-1700 nm range. In one example, IR illuminator 151 generates monochromatic light centered around 680 nm. In one example, IR illuminator 151 generates monochromatic light centered around 850 nm. The infrared illuminator 151 is disposed to direct the infrared illumination signal 152 into the diffuse medium 130. In the context of tissue, infrared illumination signal 152 will be significantly scattered within tissue within as little as 1 cm of depth into the tissue when tissue is the diffuse medium 130. At least a portion of the infrared illumination signal 152 will encounter voxel 133, as illustrated in FIG. 1A.

System 100 also includes directional ultrasonic emitter 115. Directional ultrasonic emitter 115 is configured to focus an ultrasonic signal 117 to a point in three-dimensional space. In the medical context, directional ultrasonic emitter 115 is configured to focus an ultrasonic signal 117 to a voxel within the human body. The voxel may be within the brain, abdomen, or uterus, for example. Processing logic 101 is coupled to drive directional ultrasonic emitter 115 to focus ultrasonic signal 117 to different locations in three-dimensional space via output X1, in the illustrated embodiment. The directional ultrasonic emitter 115 can be driven to focus an ultrasonic signal to voxel 133 in three-dimensional diffuse medium 130, for example. Focusing an ultrasonic signal 117 to a given voxel of tissue (e.g. voxel 133) influences the portion of infrared illumination signal 152 that encounters the voxel by wavelength-shifting at least a portion of infrared illumination signal 152 that propagates through that voxel.

In FIG. 1B, the wavelength-shifted portion of the infrared illumination signal 152 is illustrated as shifted voxel exit signal 143 generated by ultrasonic signal 117 wavelength-shifting infrared illumination signal 152 propagating through voxel 133. Being influenced by ultrasonic signal 117, shifted signal 143 has a different wavelength (hereinafter referred to as lambda-two) than infrared illumination signal 152 (referred to as lambda-one). In some embodiments, the delta between lambda-one and lambda-two may be less than 100 femtometers. In an embodiment, the delta between lambda-one and lambda-two may be less than 20 femtometer.

FIG. 1B illustrates optional filter 173 for blocking ambient light (e.g. visible light) from entering optical structure 180 while passing both shifted voxel exit signal 143 and unshifted infrared exit signal 142. FIG. 1B illustrates that optical structure 180 receives example unshifted infrared exit signal rays 141 which includes the unshifted infrared illumination signal 152 (propagating through voxels other than voxel 133) exiting diffuse medium 130. Since the unshifted infrared exit signal rays 141 are unshifted by ultrasonic signal 117, they retain the lambda-one wavelength of infrared illumination signal 152. FIG. 1B illustrates a relatively sparse amount of rays 141A, 141B, 141C, and 141D of unshifted infrared exit signal rays 141 from other voxels for clarity of illustration, although in practice, unshifted infrared exit signal rays 141 from every voxel may be received by system 100. Unshifted infrared exit signal 142 represents the unshifted lamda-one wavelength infrared light of the infrared illumination light 152 scattered by voxels of diffuse medium 130 that exits diffuse medium 130 into optical structure 180. Optical structure 180 also receives shifted voxel exit signal 143.

Unshifted infrared exit signal 142 propagates through beam splitter 153 and interferes with the portion of infrared reference beam 157 that is reflected toward imaging module 160 by beam splitter 153. Infrared reference beam 157 is generated by reference wavefront generator 155. Infrared reference beam 157 is directed toward beam splitter 153 and a portion of the infrared reference beam 157 is then directed to imaging module 160 and the remaining portion (not illustrated) passes through beam splitter 153. Imaging module 160 captures a holographic infrared image 191 of the interference of the infrared reference beam 157 and the unshifted infrared exit signal 142 that propagates through beam splitter 153. Holographic infrared image 191 may be provided to processing logic 101 via communication link X5. Optical structure 180 is configured to facilitate an interference of infrared reference beam 157 and received infrared light (e.g. signal 142).

Optical structure 180 may be configured to only receive a narrow-band infrared wavelength of infrared illumination light 152 while blocking all other light wavelengths.

FIG. 1C illustrates imaging module 160 capturing a base holographic infrared image 192 while ultrasonic signal 117 is not directed to voxel 133. The loss of light from the holographic infrared image compared to the base holographic infrared image 192 can generate a difference signal for voxel 133 that can then become a voxel value for voxel 133 in a composite image of diffuse medium 130. Throughout this disclosure, a "base holographic infrared image" will refer to a holographic infrared image captured while ultrasonic signal 117 is not propagating through a diffuse medium while a "holographic infrared image" will refer to a holographic infrared image captured while ultrasonic signal 117 is propagating through a diffuse medium and directed to (or focused to) a particular voxel in the diffuse medium.

To capture the base holographic infrared image 192, infrared illuminator 151 illuminates diffuse medium 130 with infrared illumination light 152, as shown in FIG. 1A. FIG. 1C illustrates that when ultrasonic signal 117 is not directed to (or focused to) voxel 133, the infrared light scattered by voxel 133 remains unshifted and the same wavelength (lambda-one) as infrared illumination light 152. Therefore, unshifted voxel exit signal 145 and unshifted infrared exit signal rays 141 enter optical structure 180. Base infrared exit signal 144 includes both unshifted voxel exit signal 145 and unshifted infrared exit signal rays 141 from the other voxels in diffuse medium 130. At least a portion of base infrared exit signal 144 propagates through beam splitter 153 to interfere with the portion of infrared reference beam 157 that is reflected back toward imaging module 160. Therefore, the base holographic infrared image 192 is representative of an interference of the infrared reference beam 157 with unshifted voxel exit signal 145 and unshifted infrared exit rays 141.

The base holographic infrared image 192 may be captured immediately before or immediately after holographic infrared image 191. In some embodiments, a base holographic infrared image 192 is captured and a series of infrared images are captured corresponding to different voxels in diffuse medium 130. For each different holographic infrared image, directional ultrasonic emitter 115 focuses ultrasonic signal 117 to a different voxel. As a result, each holographic infrared image in the series corresponds to the loss of light of shifted voxel exit signal 143 generated from ultrasonic signal 117 propagating through the particular voxel. Therefore, by capturing holographic infrared images while directional ultrasonic emitter 115 is scanned to focus ultrasonic signal to different voxels, voxel values for each voxel in diffuse medium 130 can be generated. A base holographic infrared image 192 may be captured periodically to refresh the base holographic infrared image that the other holographic infrared images (captured with the ultrasonic signal 117 propagating through diffuse medium) is compared to.

System 100 may refocus directional ultrasonic emitter 115 to different voxels of diffuse medium 130 and repeat the processes disclosed herein to raster scan diffuse medium 130 in order to generate a three-dimensional image of diffuse medium 130. Each voxel (e.g. voxel 133) may be imaged multiple times (with multiple corresponding measurements of signals 142 and 144) so that biological changes in voxel 133 may be recorded over a time range.

Unshifted infrared exit signal 142 for a high-absorption voxel will be stronger (have a higher intensity) than the unshifted infrared exit signal 142 for a voxel with very low absorption properties that had the same position. This means that the smaller the difference between the base holographic infrared image and a holographic infrared image associated with a particular voxel (where the ultrasonic signal is directed to that particular voxel), the higher absorption that voxel has. The larger a difference between the base holographic infrared image and the holographic infrared image associated with a particular voxel, the lower absorption that voxel has. This is because the ultrasonic signal can wavelength-shift more of the infrared illumination light 152 to the shifted voxel exit signal 143 (lambda-two) when the voxel has lower absorption and thus more infrared illumination light 152 to wavelength-shift. The more of infrared illumination light 152 shifted into signal 143 results in a weaker unshifted infrared exit signal 142 and thus a greater difference between the base holographic infrared image and the holographic infrared image for that voxel.

An input optic 147 may optionally be included in system 100. Input optic 147 may receive signal 142 and direct signal 142 to be incident on image pixel array 170. In one embodiment, input optic 147 is configured to filter out an angled portion of the signal 142. In one embodiment, the angled portion of the signal 142 has a plus-or-minus angle of incidence upon the input optic 147 that is higher than an angle threshold. In one embodiment, the angle threshold is between five and seven degrees.

Reference wavefront generator 155 generates an infrared reference beam 157 having the lambda-one wavelength so that infrared reference beam 157 interferes with the incoming base infrared exit signal 144 (to capture base holographic infrared image 192) or unshifted infrared exit signal 142 (to capture holographic infrared image(s) 191). Reference wavefront generator 155 may include one or more lasers and corresponding optics to generate a substantially uniform wavefront for infrared reference beam 157. Reference wavefront generator 155 may receive infrared light from a same laser that provides infrared light to infrared illuminator 151, in some embodiments.

In one embodiment, reference wavefront generator 155 is disposed to effect delivery of the infrared reference beam 157 to the image pixel array 170 at an angle to a pixel plane of the image pixel array 170. Image pixel array 170 may include image pixels disposed in two-dimensional rows and columns that define the pixel plane of the image pixel array 170. Processing logic 101 is coupled to initiate the image capture by image pixel array 170 via output X5, in the illustrated embodiment.

A linear polarizer may be included in system 100 to polarize signals 142/144 to have the same polarization orientation as infrared reference beam 157. The light source provided to reference wavefront generator 155 may generate linear polarized light which imparts a polarization orientation to infrared reference beam 157. The linear polarizer may be included in optic 147, filter 173, or in a linear polarizer disposed between optic 147 and filter 173, for example.

Image pixel array 170 may be implemented with an a-Si (amorphous Silicon) thin film transistors or a CMOS (Complementary Metal-Oxide-Semiconductor) image sensor, in some embodiments. Image pixel array 170 can be a commercially available image sensor. In one embodiment, image pixel array 170 has image pixels having a pixel pitch of 3.45 microns. In one embodiment, image pixel array 170 has image pixels having a pixel pitch of 1.67 microns. The pixel resolution of image pixel array 170 may vary depending on the application. In one embodiment, the image pixel array 170 is 1920 pixels by 1080 pixels. In one embodiment, the image pixel array is 40 Megapixels or more. Image pixel array 170 can capture an infrared image of an interference pattern between signals 142/144 and infrared reference beam 157 by measuring the image charge generated in each pixel during a given integration period that is determined by an electronic shutter. The electronic shutter may be a global shutter (where each pixel measures the incident light during a same time period) or a rolling shutter. The electronic shutter can be actuated by processing logic 101 via input/output X5. Input/output X5 may include digital input/output lines as well as a data bus. Image pixel array 170 may include a local (on-board) digital signal processor (DSP), in some embodiments, and processing logic 150 may receive the captured infrared images from the DSP.

Processing logic 101 may include a processor, microprocessor, cluster of processing cores, FPGA (field programmable gate array), and/or other suitable combination of logic hardware. In some embodiments, memories (not illustrated) are integrated into the processing logic to store instructions to execute operations and/or store data. An external memory or memories (not illustrated) may also be coupled to processing logic 101 to store instructions to execute operations and/or store data. A "memory" or "memories" described in this disclosure may include volatile or non-volatile memory architectures. Processing logic 101 may be configured to execute operations including (1) capturing first data (e.g. holographic infrared image) from a sensor (e.g. sensor in imaging module 160) while an infrared illumination signal illuminates a diffuse medium and an ultrasonic signal (e.g. 117) is propagating through the diffuse medium; (2) capturing second data (e.g. base holographic infrared image) from the sensor while the infrared illumination signal illuminates the diffuse medium and the ultrasonic signal is not propagating through the diffuse medium; and (3) generating a difference signal based on the second data and the first data.

Processing logic 101 may be configured to execute further operations including incorporating the difference signal as a voxel value in a composite image of the diffuse medium. The difference signal may represent a drop in the received infrared light interfering with the infrared reference beam due to the ultrasonic signal wavelength-shifting the infrared illumination signal outside of the narrow-band infrared wavelength that is received by the optical structure (e.g. optical structure 180).

In an embodiment, an ultrasonic emitter (e.g. 115) is configured to direct a series of ultrasonic signals to a series of voxels corresponding with image pixel array 170 capturing the interferences of the infrared reference beam with the infrared exit signal for each voxel. Processing logic 101 may be configured to drive the ultrasonic emitter and image pixel array 170 to coordinate the scanning of the ultrasonic signal 117 to particular voxels and capturing the holographic infrared image for that voxel while the ultrasonic signal is focused to the voxel. Processing logic 101 may be configured to generate a series of intensity values corresponding to the series of voxels where each intensity value is generated based on a difference between the base holographic infrared image and a particular holographic infrared image corresponding with a particular voxel in the series of voxels.

Figure 2A:
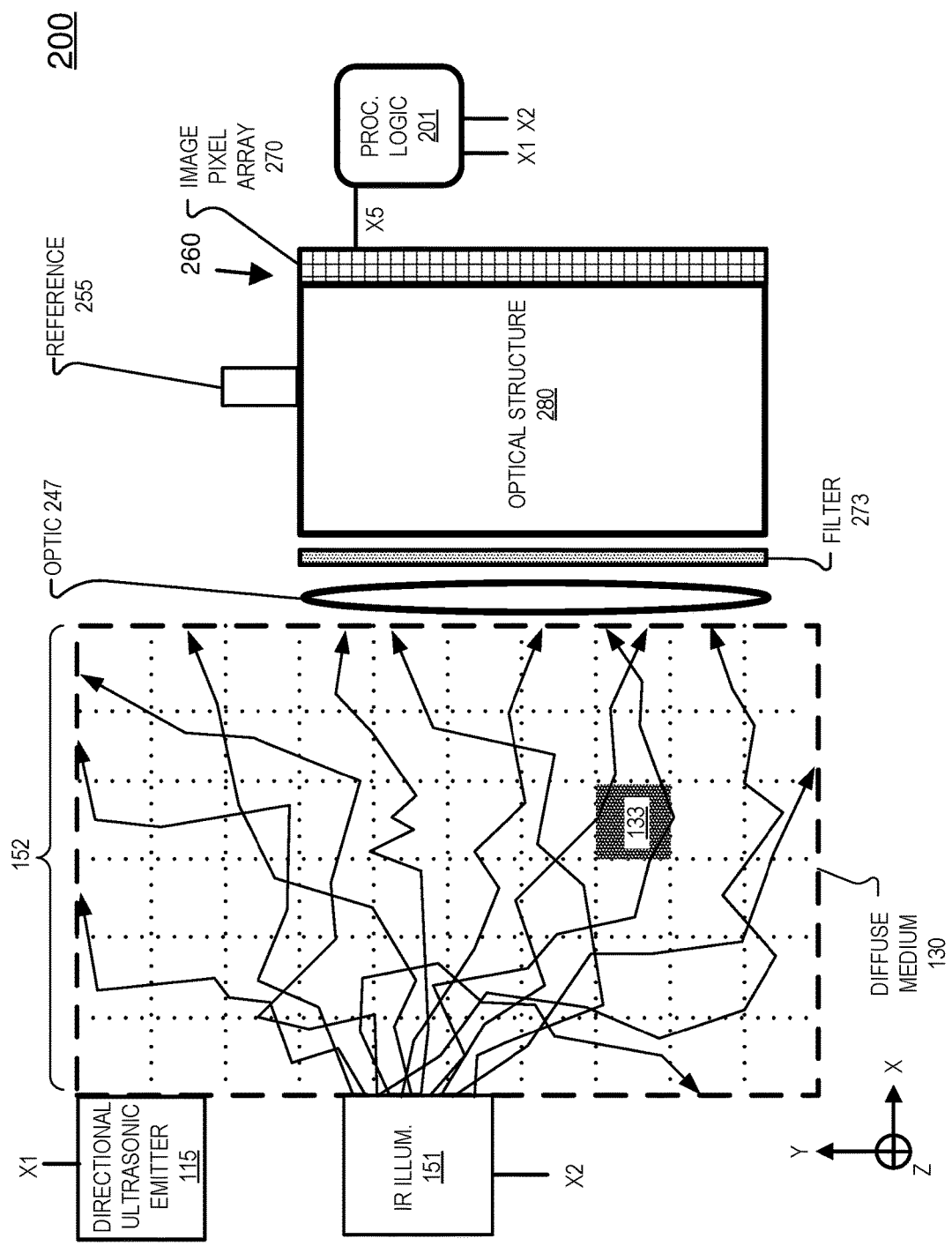
FIGS. 2A-2C illustrate an example imaging system that includes an example optical structure and an example imaging module, in accordance with an embodiment of the disclosure.
Figure 2B:
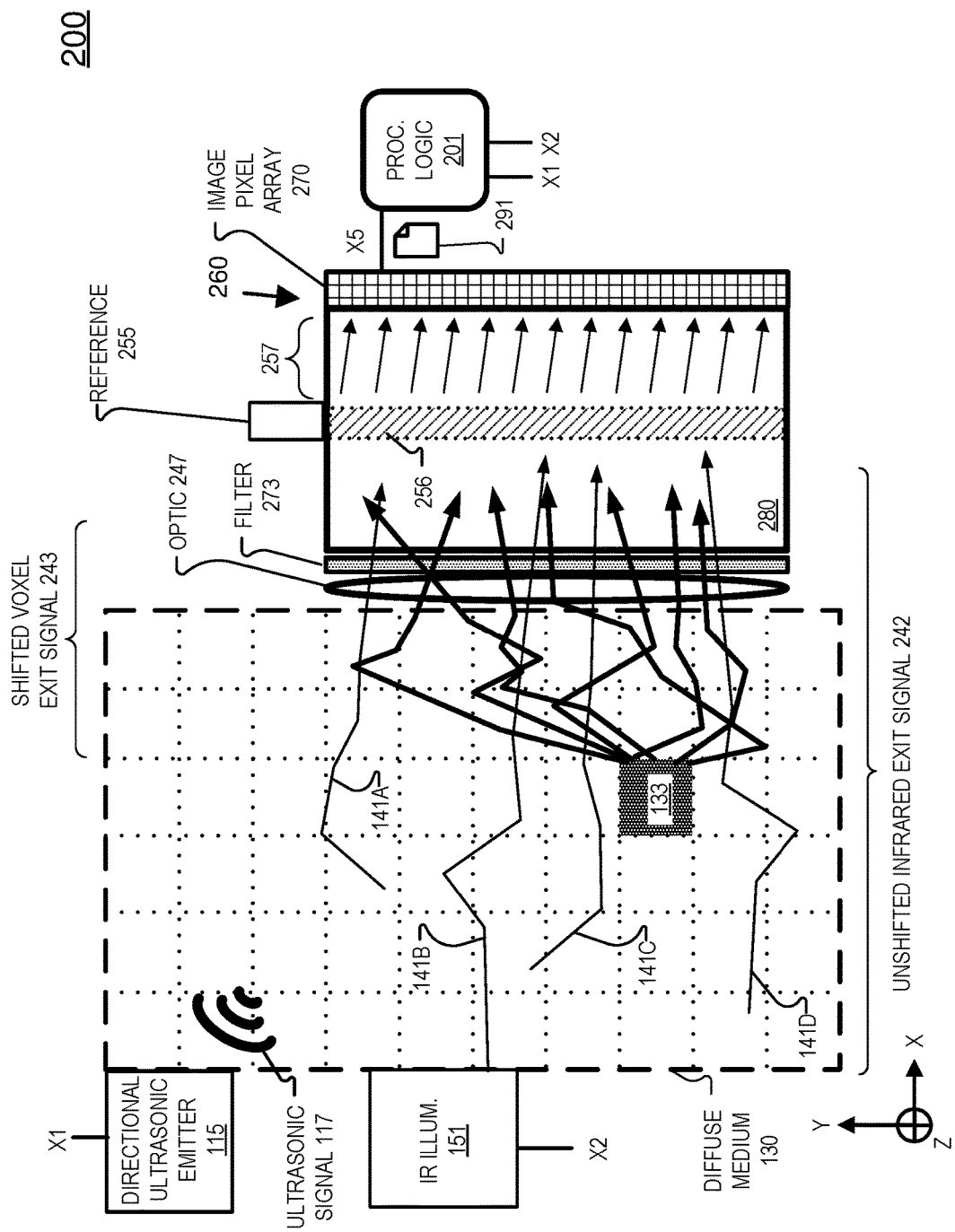
Figure 2C:
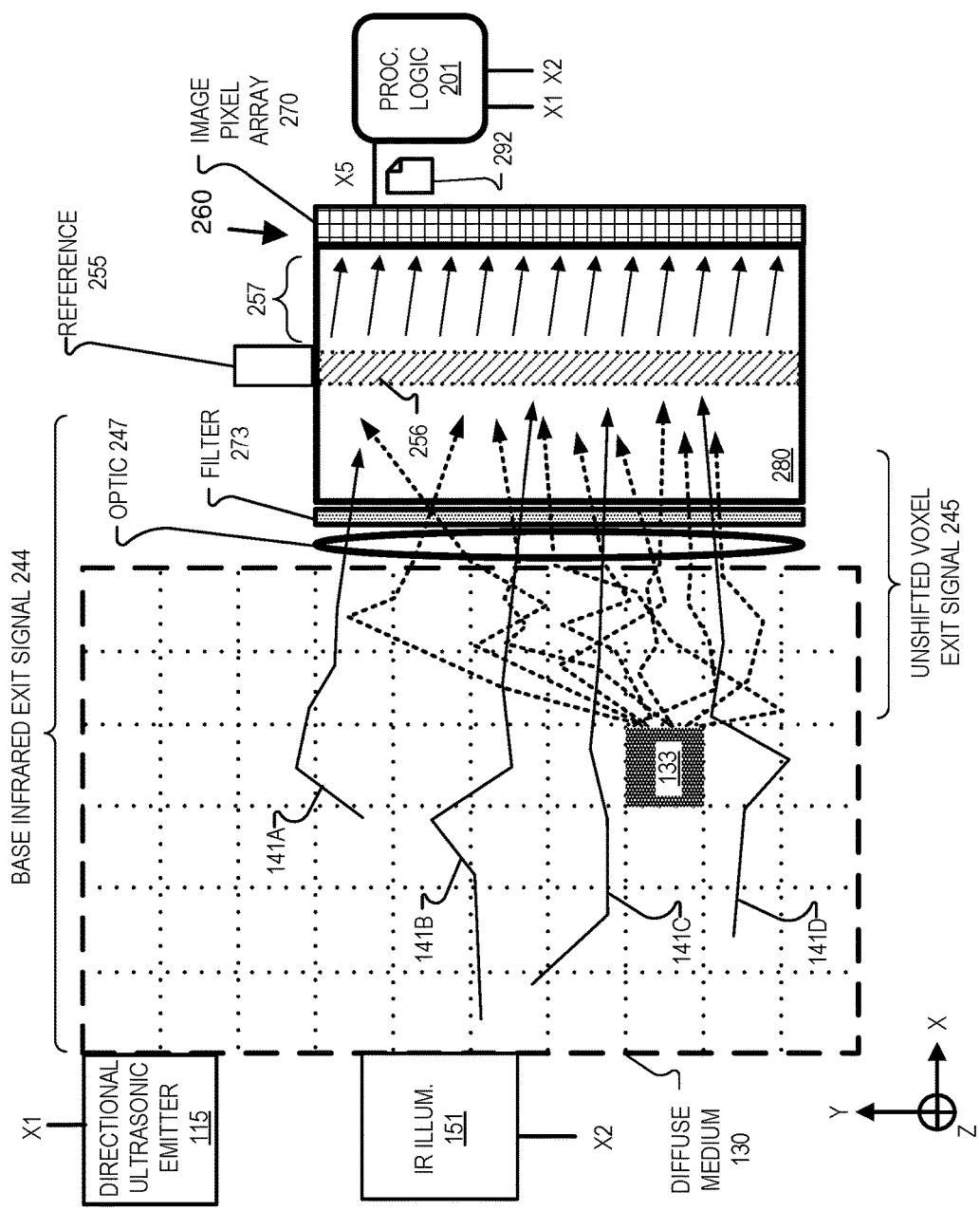

FIGS. 2A-2C illustrate an example imaging system 200 that includes an example optical structure 280 and an imaging module 260, in accordance with an embodiment of the disclosure. System 200 illustrated in FIGS. 2A-2C functions similarly to system 100 of FIGS. 1A-1C although optical structure 280 is of a different configuration than optical structure 180.

Similarly to FIG. 1A, in FIG. 2A, processing logic 201 is coupled to drive directional ultrasonic emitter 115 to focus ultrasonic signal 117 to different locations in three-dimensional space (e.g. diffuse medium 130), via output X1. Processing logic 201 is also coupled to selectively activate IR illuminator 151 via output X2, in the illustrated embodiment. Imaging module 260 includes image pixel array 270 and may include further optical components such as lenses or filters (not specifically illustrated). Image pixel array 270 may be configured similarly to image pixel array 170. Optic 247 may be configured similarly to optic 147 and filter 273 may be configured similarly to filter 173.

Processing logic 201 may include a processor, microprocessor, cluster of processing cores, FPGA (field programmable gate array), and/or other suitable combination of logic hardware. In some embodiments, memories (not illustrated) are integrated into the processing logic to store instructions to execute operations and/or store data. An external memory or memories (not illustrated) may also be coupled to processing logic 201 to store instructions to execute operations and/or store data. A "memory" or "memories" described in this disclosure may include volatile or non-volatile memory architectures.

As in FIG. 2A, infrared illuminator 151 is driven to generate infrared illumination signal 152 that illuminates diffuse medium 130 and scatters within diffuse medium 130. FIG. 2B illustrates that optical structure 280 differs from optical structure 180 in that reference director optic 256 directs infrared reference beam 257 to image pixel array 270 rather than beam splitter 153. Reference port 255 is configured to selectively emit an infrared reference light having the lambda-one wavelength so that infrared reference beam 257 interferes with the unshifted infrared exit signal 242 (in FIG. 2B) and base infrared exit signal 244 (FIG. 2C) that also have the lambda-one wavelength. Reference port 255 may include one or more laser diodes or receive the infrared reference beam from a laser through a fiber optic, for example. Reference director optic 256 in optical structure 280 may direct the lambda-one infrared reference beam to image pixel array 270 as a substantially uniform infrared reference wavefront. Reference director optic 256 may be a planar beam splitter or a partially reflective surface disposed on a curved structure. In an embodiment, reference director optic 256 includes a diffractive optical structure that is angle-selective and wavelength-selective to direct infrared reference beam 257 received from reference port 255 to imaging module 260.

FIG. 2B illustrates optional filter 273 for blocking ambient light from entering optical structure 280 while passing both shifted voxel exit signal 243 and unshifted infrared exit signal 242. FIG. 2B also illustrates that optical structure 280 receives unshifted infrared exit signal rays 141 which includes the unshifted infrared illumination signal 152 (propagating through voxels other than voxel 133) exiting diffuse medium 130. Since the unshifted infrared exit signal rays 141 are unshifted by ultrasonic signal 117, it retains the lambda-one wavelength. FIG. 2B illustrates a relatively sparse amount of rays 141A, 141B, 141C, and 141D of example unshifted infrared exit signal rays 141 from other voxels for clarity of illustration, although in practice, rays of unshifted infrared exit signal rays 141 from every voxel may be received by system 200. Optical structure 280 also receives shifted voxel exit signal 243.

Imaging module 260 captures a holographic infrared image 291 of the interference of the infrared reference beam 257 and the unshifted infrared exit signal 242 that propagates through reference director optic 256. Holographic infrared image 291 may be provided to processing logic 201 via communication link X5.

To capture the base holographic infrared image 292 in FIG. 2C, infrared illuminator 151 illuminates diffuse medium 130 with infrared illumination light 152, as shown in FIG. 2A. FIG. 2C illustrates that when ultrasonic signal 117 is not directed to (or focused to) voxel 133, the infrared light scattered by voxel 133 remains unshifted and the same wavelength as infrared illumination light 152. Therefore, unshifted voxel exit signal 245 and unshifted infrared exit signal rays 141 enter optical structure 280. Base infrared exit signal 244 includes both unshifted voxel exit signal 245 and unshifted infrared exit signal rays 141 from the other voxels in diffuse medium 130. At least a portion of base infrared exit signal 244 propagates through reference director optic 256 to interfere with the portion of infrared reference beam 257 that is directed toward imaging module 260. Therefore, the base holographic infrared image 292 is representative of an interference of the infrared reference beam 257 with unshifted voxel exit signal 245 and unshifted infrared exit rays 141.

A linear polarizer may be included in system 200 to polarize signals 242 and 244 to have the same polarization orientation as infrared reference beam 257. Reference port 255 may provide linear polarized light which imparts a polarization orientation to infrared reference beam 257. The linear polarizer may be included in optic 247, filter 273, or optical structure 280.

In one embodiment, reference director optic 256 is configured to deliver the infrared reference beam 257 to the image pixel array 270 at an angle to a pixel plane of the image pixel array 270. Processing logic 201 is coupled to initiate the image capture by image pixel array 270 via output X5, in the illustrated embodiment.

Figure 3:
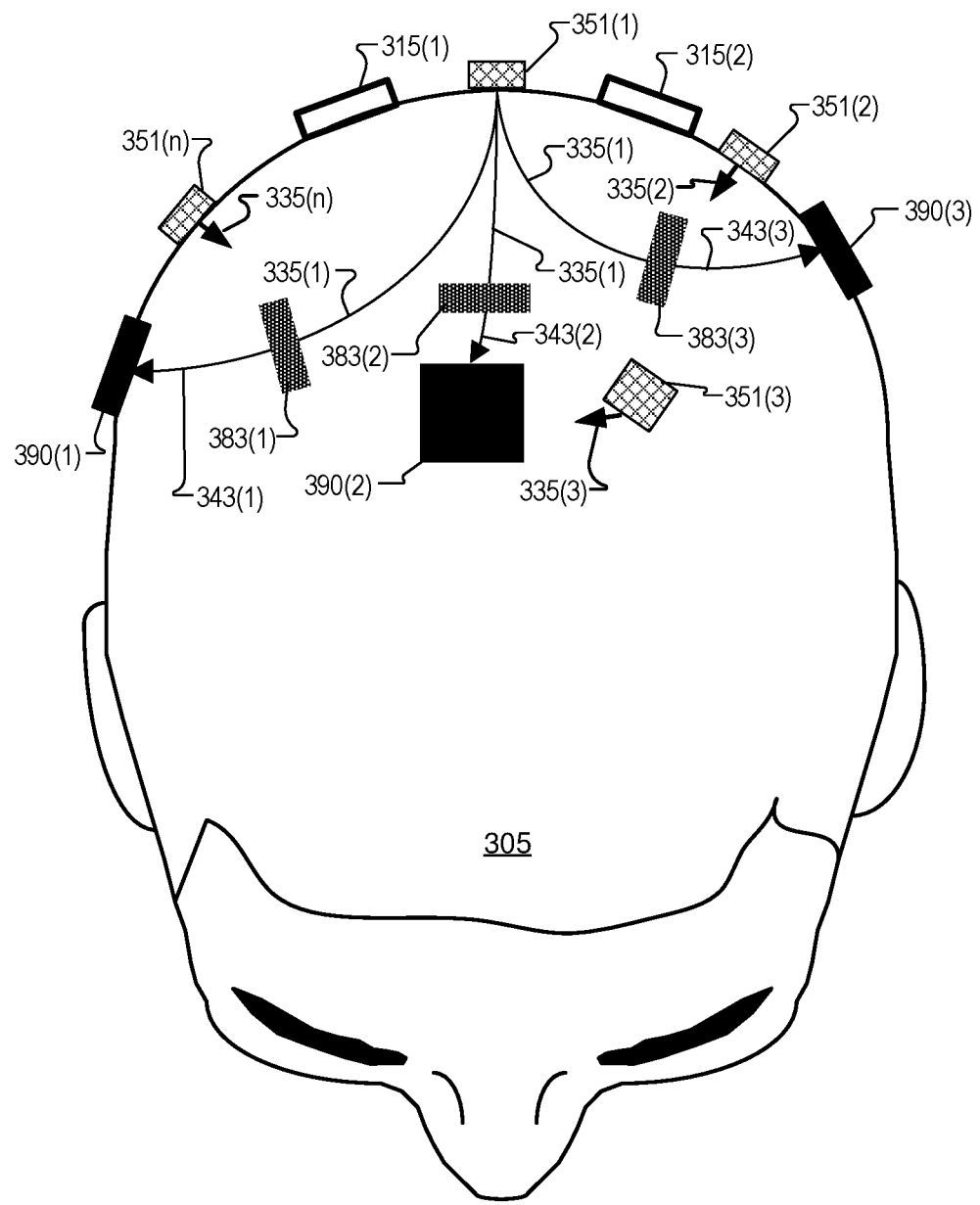
FIG. 3 illustrates an example placement of components of an imaging system with respect to a human head, in accordance with an embodiment of the disclosure.

FIG. 3 illustrates an example placement of components of an imaging system 300 with respect to a human head 305, in accordance with aspects of the disclosure. FIG. 3 is a top-down view of a human head 305. Imaging system 300 includes infrared illuminators 351, imaging modules 390, and directional ultrasonic emitters 315. Imaging modules 390 may include the features of imaging module 160/260 and optical structure 180/280. Ultrasonic emitters 315 may include the features of directional ultrasonic emitter 115. FIG. 3 shows that infrared illumination light 335 is directed into head 305 by one or more infrared illuminators 351. An optical fiber may be used to route the light 335 from a common light source (e.g. an infrared laser) to particular output positions with respect to head 305. In some embodiments, infrared illuminators 351 are spatially positioned on head 305 in positions so that each imaging module 390 is equidistant to the infrared illuminators 351.

The example optical paths of infrared illumination light 335(1) through voxels 383 is illustrated in FIG. 3, although the optical paths of infrared illumination light 335(2), 335 (3), and 335(n) are not illustrated. Of course, in operation, the optical paths of light 335(1) to voxels 383 will not be as direct as the illustration because it will encounter voxels 383 via random scattering of the tissue.

Infrared illumination light 335(1) outputted by infrared illuminator 351(1) scatters in head 305 and a portion encounters voxel 383(1). Light 335(2), 335(3) . . . through 335(n) may also illuminate voxel 383(1). One or more of ultrasonic emitters 315 may focus their ultrasound signal (not illustrated) to voxel 383(1) which generates a shifted voxel exit signal 343(1) of the light 335 that illuminated voxel 383(1). Shifted voxel exit signal 343(1) is lambda-two wavelength light. Imaging module(s) 390 may capture a holographic infrared image of an interference pattern generated by exit signal 343(1) interfering with an infrared reference beam to generate a measurement of the absorption of voxel 383(1) to light 335. The imaging module 390 may also capture a base holographic infrared image of voxel 383(1) (while ultrasonic emitter(s) 315 are deactivated) to compare to the holographic infrared image. FIG. 3 illustrates that imaging module(s) 390 may also capture images of an interference pattern generated by exit signal 343(2) interfering with an infrared reference beam (e.g. 157/257) to generate a measurement of the absorption of voxel 383(2) to light 335 and imaging module(s) 390 may also capture images of an interference pattern generated by exit signal 343(3) interfering with an infrared reference beam to generate a measurement of the absorption of voxel 383(3) to light 335.

Scientific literature suggests that the penetration depth of infrared light into tissue is around 10 cm so multiple imaging modules 390 may be needed to image the entire brain or other tissue. A wearable hat may include system 300 so that system 300 can be worn as a wearable, in some embodiments. Other wearables may also include all or part of system 300.

Although not specifically illustrated in FIGS. 1A-2C, infrared illuminator 151 and reference wavefront generator 155 may be fiber optic outputs that are provided light via optical fibers from a single laser source. Similarly, infrared illuminator 151 and reference port 255 may be provided light via optical fibers from a single laser source.

Figure 4A:
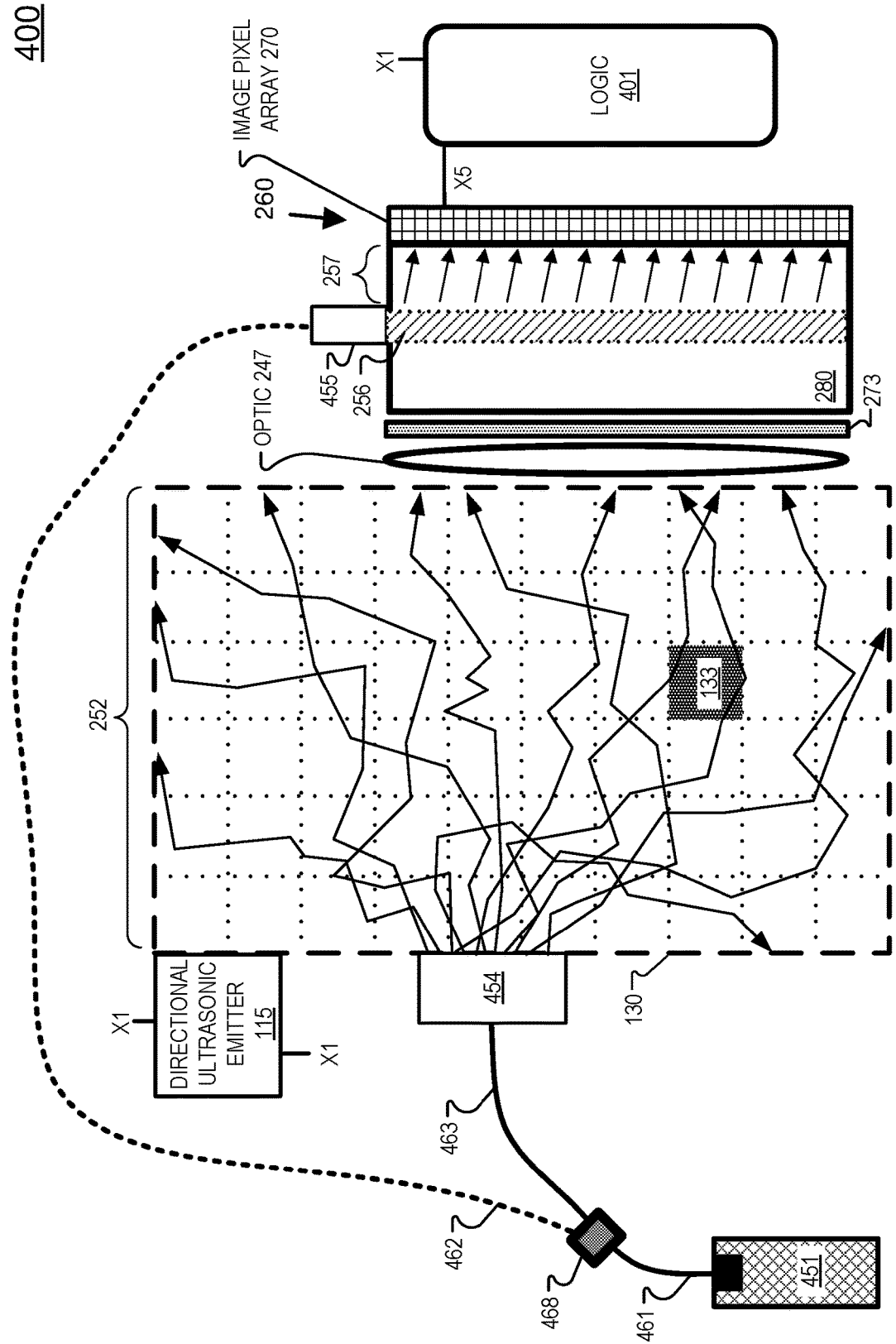
FIGS. 4A-4C illustrate an example imaging system that includes an infrared illumination aperture and a reference aperture configured to receive infrared light from the same infrared laser via optical fibers, in accordance with an embodiment of the disclosure.
Figure 4B:
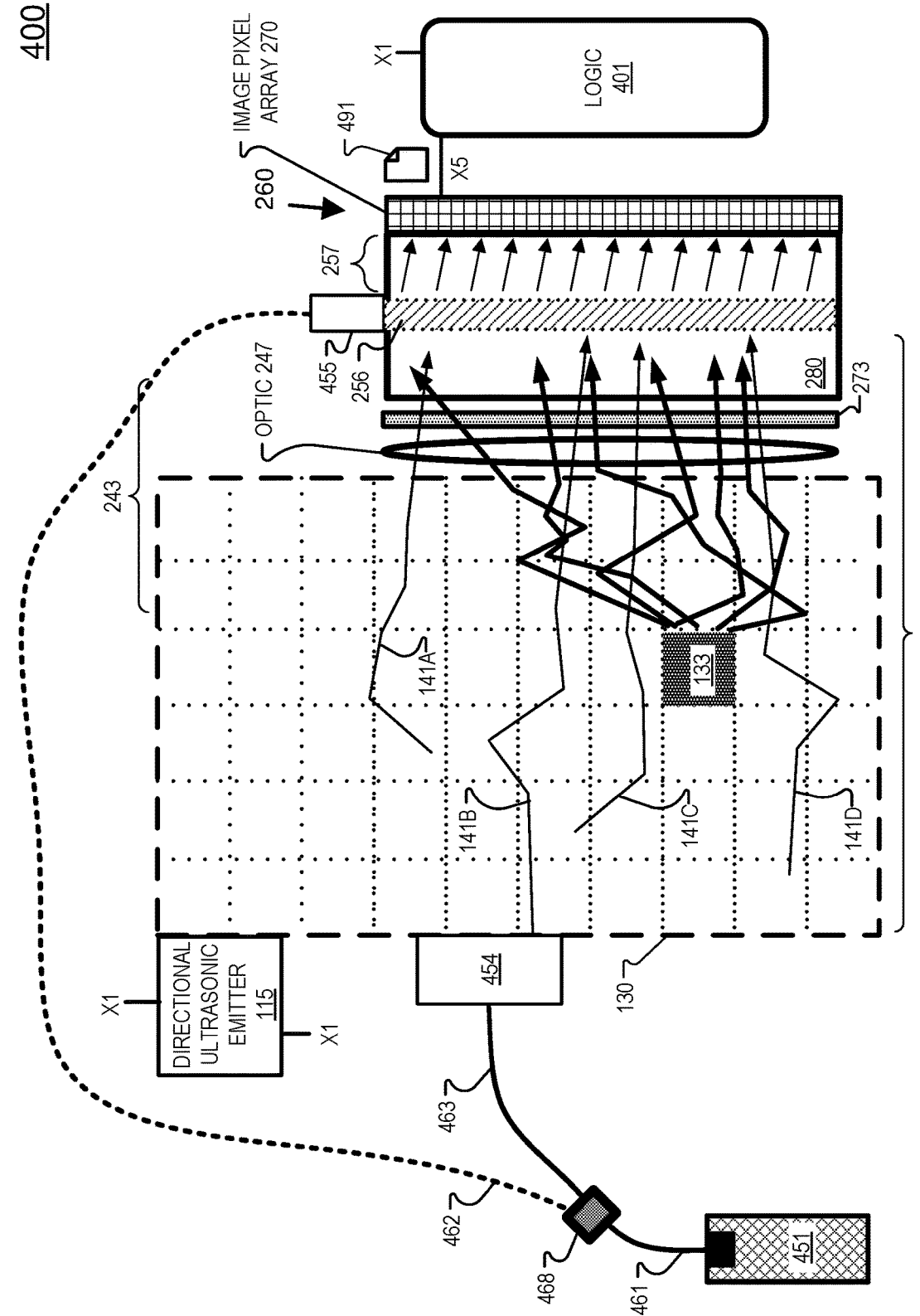
Figure 4C:
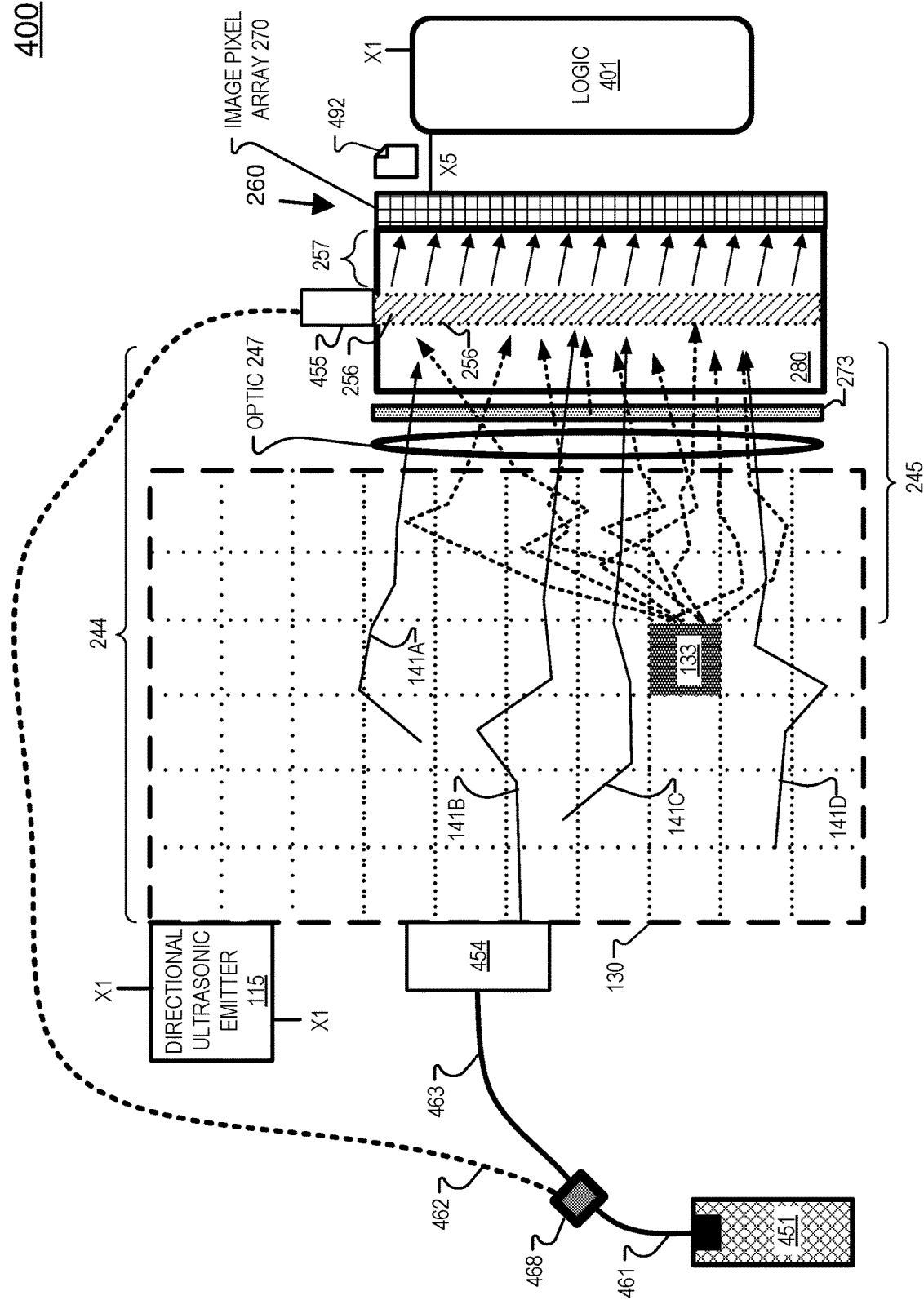

FIGS. 4A-4C illustrate an example imaging system 400 that includes an infrared illumination aperture 454 and a reference aperture 455 configured to receive infrared light from the same infrared laser via optical fibers, in accordance with an embodiment of the disclosure. In operation, system 400 functions similarly to system 200. FIG. 4B shows that processing logic 401 is coupled to drive directional ultrasonic emitter 115 to focus ultrasonic signal 117 to different locations in three-dimensional space, via communication channel X1. Processing logic 401 may be coupled to initiate an infrared image capture by image pixel array 270 via output X5, in FIGS. 4A-4C. Logic 401 may also be coupled to receive the captured infrared image from the image pixel array 270. For example, in FIG. 4B, logic 401 receives a holographic infrared image 491 and in FIG. 4C, logic 401 receives a base holographic infrared image 492. Logic 401 may be configured to generate a composite image of diffuse medium 430 that includes captured images (e.g. 491 and 492) corresponding to different voxels of the diffuse medium 130.

Processing logic 401 may include a processor, microprocessor, cluster of processing cores, FPGA (field programmable gate array), and/or other suitable combination of logic hardware. In some embodiments, memories (not illustrated) are integrated into the processing logic to store instructions to execute operations and/or store data. An external memory or memories (not illustrated) may also be coupled to processing logic 401 to store instructions to execute operations and/or store data. A "memory" or "memories" described in this disclosure may include volatile or non-volatile memory architectures.

Light source 451 may be an infrared laser configured to emit infrared light, in some embodiments. Light source 451 may be a pulsed infrared laser configured to emit pulsed infrared light, in some embodiments. A pulsed infrared laser may emit an infrared pulse having a pulse width of approximately 100-250 nanoseconds, at a frequency of 360 Hz. or greater, and having an energy of approximately 15-150 mJ per pulse. In some embodiments, the infrared illumination signal generated by light source 451 may have a narrowband infrared wavelength centered around 725 nm, 825 nm, 1064 nm, or 1450 nm, for example.

The infrared illumination signal emitted from light source 451 is emitted into optical fiber 461, in FIG. 4A. A beam directing component 468 may divert the infrared illumination signal between optical fiber 462 and 463. Beam directing component 468 may be a beam splitter. Beam directing component 468 may be an active component configured to be modulated (e.g. an acoustic optical modulator) to direct the proper proportions of infrared illumination signal propagating through fiber optic 461 to the proper fiber optic 462 or 463. A micro-electro-mechanical system (MEMS) mirror, a digital micromirror device (DMD), or a mirror galvanometer may be used to selectively couple light from optical fiber 461 into different fiber optic paths, in different embodiments. The light from light source 451 is lambda-one wavelength light.

Reference aperture 455 receives the infrared illumination signal from optical fiber 462 and provides the infrared illumination signal to optical structure 280 as the infrared reference beam. Illumination aperture 454 is configured to receive the infrared illumination light from optical fiber 463 and provide the infrared illumination light to diffuse medium 130 as the infrared illumination light.

Figure 5:
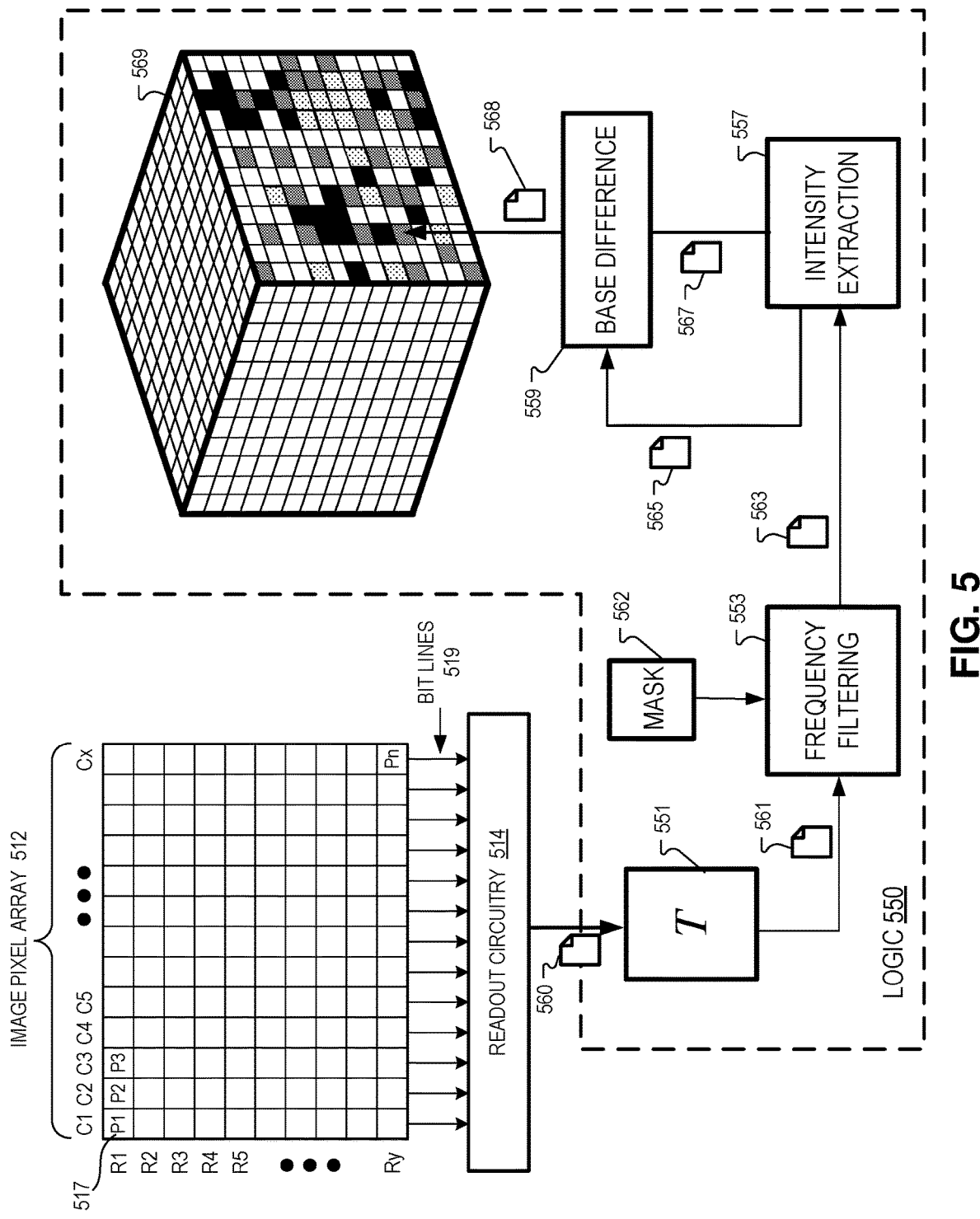
FIG. 5 illustrates an image pixel array coupled to example processing logic, in accordance with an embodiment of the disclosure.

FIG. 5 illustrates an image pixel array 512 coupled to example processing logic 550, in accordance with an embodiment of the disclosure. Processing logic 550 may be included in processing logic 401, in some embodiments. Image pixel array 512 includes image pixels 517 arranged in integer number x columns and integer number y rows. Readout circuitry 514 is coupled to read the signal value from image pixels 517 via bitlines 519. Image pixel array 512 may be a complementary metal-oxide-semiconductor (CMOS) image pixel array. Image pixel array 512 may be an example of image pixel array 170/270 and be included in an image sensor.

Transform engine 551 in logic 550 is coupled to receive exit signal data 560 from readout circuitry 514, in FIG. 5. Exit signal data 560 may include one or more images including the interference pattern generated by signal 142/144 interfering with infrared reference beam 157 or signal 242/244 interfering with infrared reference beam 257. Exit signal data 560 may include base holographic infrared images 192, 292, and/or 492, and holographic infrared images 191, 291, and/or 491. In some embodiments, transform engine 551 may be configured to receive exit signal data 560 from processing logic 101, 201, or 401. Transform engine 551 generates a frequency domain image 561 by performing a Transform operation on an image included in exit signal data 560 received from readout circuitry 514. In one embodiment, the Transform operation includes a Fourier transform. In one embodiment, the Transform operation includes a discrete cosine transform.

Frequency filtering engine 553 is coupled to receive the frequency domain image 561 from Transform engine 551 and also coupled to receive mask 562. Frequency filtering engine 553 is configured to multiply the frequency domain infrared image 561 with the mask 562 to generate a filtered frequency domain image 563. Mask 562 is designed to isolate the frequency of the exit signal (e.g. 142/144/242/244) for further processing. Mask 562 may include a matrix that includes '1' values for the portion of the frequency domain image 561 that corresponds to the lambda-one wavelength of the exit signal(s) and '0' values for other portions of the frequency domain image 561. In one embodiment, mask 562 is a two-dimensional Gaussian filter.

Intensity extraction engine 557 is coupled to receive the filtered frequency domain image 563. Intensity extraction engine 557 may be configured to generate base intensity data 565 when exit signal data 560 includes a base holographic infrared image (e.g. 192/292/492). Intensity extraction engine 557 may provide base intensity data 565 to base difference engine 559. Intensity extraction engine 557 may also be configured to generate intensity data 567 when exit signal data 560 includes a holographic infrared image (e.g. 191/291/491) that is not a base holographic infrared image. Intensity extraction engine 557 may provide intensity data 567 to base difference engine 559. In one embodiment, generating the data 565/567 includes averaging intensity values of the filtered frequency domain image 563. In an embodiment where a Fourier transform is used as the transform operation in Transform engine 551, the Fourier coefficients are extracted from filtered frequency domain image 563 and a sum of the absolute value squared of the Fourier coefficients is calculated. The sum is then used as data 565/567.

Base difference engine 559 generates voxel value 568 based on a difference between base intensity data 565 and intensity data 567. Logic 550 may then incorporate voxel value 568 into composite image 569 as a voxel value corresponding to a particular voxel that the ultrasonic signal 117 was focused to when the holographic infrared image that generated intensity data 567 was captured. Composite image 569 is illustrated as a three-dimensional image in FIG. 5 and may be a three-dimensional image of diffuse medium. As described in this disclosure, the system 100, 200, or 400 may raster scan through diffuse medium 130 (focusing on different voxels) to generate a three-dimensional image of diffuse medium 130 using a plurality of infrared images and at least one base infrared image. System 100, 200, or 400 may refocus directional ultrasonic emitter 115 to different voxels of diffuse medium 130 and repeat the processes disclosed herein to raster scan diffuse medium 130 in order to generate a three-dimensional image (e.g. composite image 569) of diffuse medium 130.

Image 569 may represent absorption properties of a diffuse medium on a voxel-by-voxel basis. The comparison of absorptions of different voxels may generate an image that shows a concentration of voxels that have high absorption properties. A grouping of high absorption voxel may indicate increased blood flow in the region, for example. Scanning the directional ultrasound emitter (e.g. 115) to different voxels allows the system to generate voxel values for each voxel in the diffuse medium.

Figure 6:
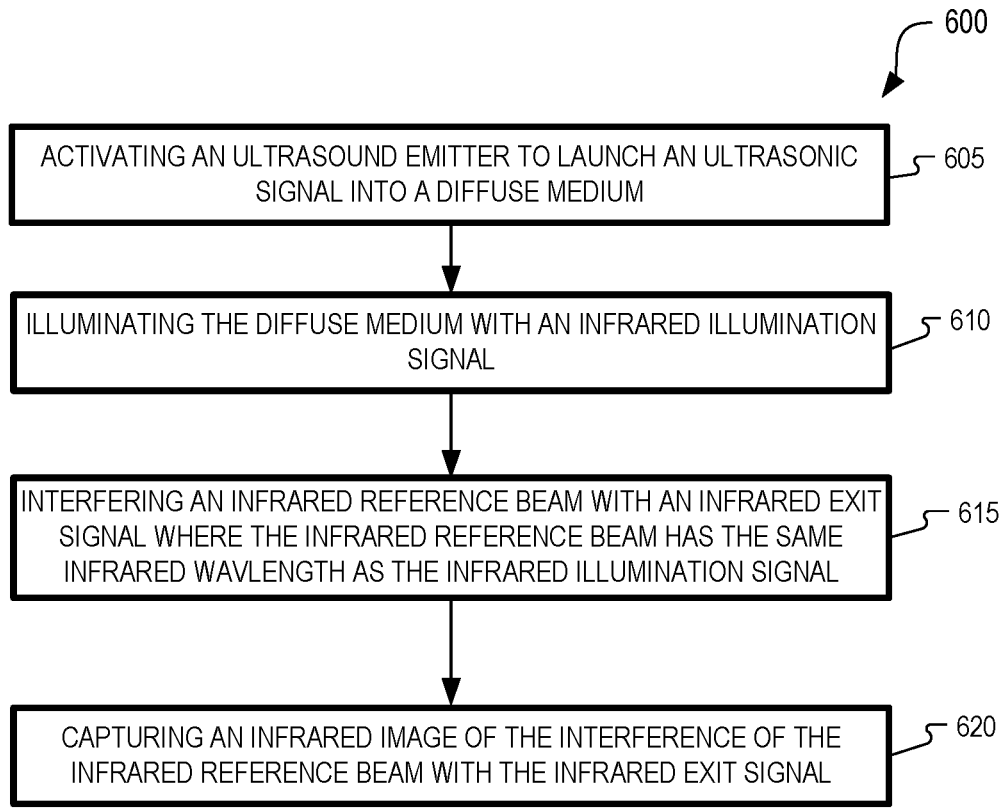
FIG. 6 illustrates an example flow chart of a process of capturing infrared images of an infrared exit signal, in accordance with an embodiment of the disclosure.

FIG. 6 illustrates an example flow chart of a process 600 of capturing infrared images of an infrared exit signal, in accordance with an embodiment of the disclosure. The order in which some or all of the process blocks appear in process 600 should not be deemed limiting. Rather, one of ordinary skill in the art having the benefit of the present disclosure will understand that some of the process blocks may be executed in a variety of orders not illustrated, or even in parallel. Processing logic 101, 201, or 401 may execute some or all of the operations of process 600, for example.

In process block 605, an ultrasound emitter (e.g. directional ultrasonic emitter 115) is activated (e.g. turned ON) to launch an ultrasonic signal into a diffuse medium, such as diffuse medium 130. The diffuse medium may include tissue.

In process block 610, the diffuse medium is illuminated with an infrared illumination signal (e.g. signal 152) having an infrared wavelength. The infrared illumination signal may be near-infrared light.

In process block 615, an infrared reference beam (e.g. 157/257) is interfered with an infrared exit signal. The infrared exit signal is in the infrared illumination signal exiting the diffuse medium. The infrared reference beam has the same infrared wavelength as the infrared illumination signal.

In process block 620, an infrared image of the interference of the infrared reference beam and the infrared exit signal is captured. For example, image pixel array 170 or 270 may capture an infrared image of the interference of the infrared reference beam and the infrared exit signal (e.g. 142 or 242). The infrared image may be captured with an image sensor, for example.

The infrared image captured in process block 620 may be captured while the ultrasonic image of process block 605 is propagating through the diffuse medium. In some embodiments, process 600 further includes illuminating the diffuse medium with a base infrared illumination signal having the infrared wavelength that is the same as the infrared reference beam. The base infrared illumination signal is similar to infrared illumination signal 152/252 except that it illuminates the diffuse medium at a time different than when the infrared illumination signal illuminates the diffuse medium. In particular, the base infrared illumination signal illuminates diffuse medium 130 when ultrasonic signal 117 is not propagating through diffuse medium 130 and the infrared illumination signal of process 600 illuminates diffuse medium 130 while ultrasonic signal 117 is directed to a particular voxel of the diffuse medium. Process 600 may further include capturing a base infrared image while the ultrasonic signal is not propagating through the diffuse medium and while the base infrared illumination signal is propagating through the diffuse medium. The base infrared image captures an interference of the infrared reference beam with a base infrared exit signal (e.g. 144/244) that is the base infrared illumination signal exiting the diffuse medium. Process 600 may further include generating first intensity data based on the base infrared image and the infrared image where the ultrasonic signal is directed to a first voxel of the diffuse medium while the infrared image is being captured and incorporating the first intensity data as a first voxel value in a composite image (e.g. 569) of the diffuse medium—the first voxel value corresponding to a first voxel position in the composite image.

In embodiments of process 600, a same laser source may be optically coupled to generate the infrared illumination signal and the infrared reference beam. For example, FIGS. 4A-4C illustrate that light source 451 may be an infrared laser and optical fibers carry the infrared laser light from the infrared laser to aperture 454 to illuminate diffuse medium 130 with infrared illumination light and from the infrared laser to reference aperture 455 to provide the infrared reference beam to optical structure 280.

An ultrasound emitter may be configured to be directed to different voxels in the diffuse medium, in embodiments of process 600. In process 600, the infrared image captured in process block 620 may be considered a holographic infrared image.

Process 600 may also include generating first intensity data from the infrared image where the ultrasonic signal in process block 605 is focused to a first voxel of the diffuse medium while the infrared image is being captured. Process 600 may further include incorporating the first intensity data as a first voxel value in a composite image (e.g. 569) of the diffuse medium. The first voxel value corresponds to a first voxel position in the composite image.

Figure 7:
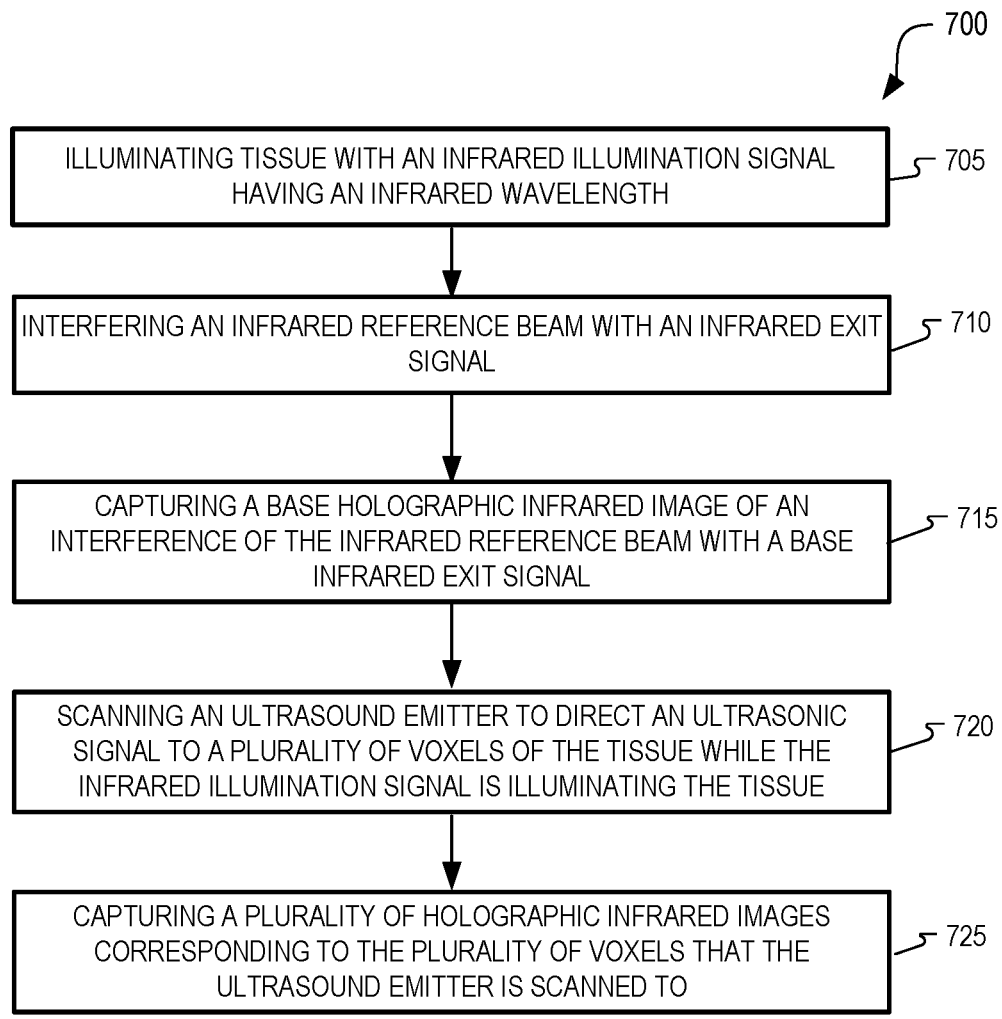
FIG. 7 illustrates an example flow chart of a process of capturing holographic infrared image(s) corresponding to voxels of a diffuse medium, in accordance with an embodiment of the disclosure.

FIG. 7 illustrates an example flow chart of a process 700 of capturing holographic infrared image(s) corresponding to voxels of diffuse medium, in accordance with an embodiment of the disclosure. The order in which some or all of the process blocks appear in process 700 should not be deemed limiting. Rather, one of ordinary skill in the art having the benefit of the present disclosure will understand that some of the process blocks may be executed in a variety of orders not illustrated, or even in parallel. Processing logic 101, 201, or 401 may execute some or all of the operations of process 700, for example.

In process block 705, an infrared illumination signal having an infrared wavelength illuminates tissue.

In process block 710, an infrared reference beam is interfered with an infrared exit signal. The infrared exit signal is the infrared illumination signal exiting the tissue and the infrared reference beam has the infrared wavelength that is the same as the infrared illumination signal.

In process block 715, a base holographic infrared image of an interference of the infrared reference beam and the base infrared exit signal is captured.

In process block 720, an ultrasound emitter is scanned to direct an ultrasonic signal to a plurality of voxels of the tissue while the infrared illumination signal is illuminating the tissue. The base holographic infrared image is captured when the ultrasonic signal is not propagating through the tissue.

In process block 725, a plurality of holographic infrared images is captured where the plurality of holographic infrared images corresponds to the plurality of voxels that the ultrasound emitter is scanned to. The plurality of holographic images captures an interference of the infrared reference beam with the infrared exit signal at a time when the ultrasonic signal is directed to a particular voxel in the plurality of voxels.

To illustrate an example implementation, a base holographic infrared image may be captured at a time $t_0$. At a time $t_1$, a first holographic infrared image in the plurality of holographic infrared images is captured. At time ti, the ultrasound emitter may be scanned to a first voxel of tissue and the ultrasonic signal is directed to or focused on the first voxel. A difference between the base holographic infrared image and the first holographic infrared image represents a loss of light generated by the ultrasonic signal focusing on the first voxel due to the ultrasonic signal wavelength-shifting the infrared illumination signal away from the wavelength of the infrared reference beam. Thus the difference between the base holographic infrared image and the first holographic infrared image represents a drop in the received infrared light interfering with the infrared reference beam.

In some embodiments, the base holographic infrared image is captured prior to the holographic infrared image(s).

In some embodiments, the holographic infrared image is captured prior to the base holographic infrared image. In some embodiments, the base holographic infrared image is captured and the plurality of holographic infrared images is compared to the same base holographic infrared image to generate a difference between a particular holographic infrared image (corresponding to a particular voxel) and the base holographic infrared image. For example, a base holographic infrared image may be captured followed by five holographic infrared images to be compared to the base holographic infrared image. Then, a refreshed base holographic infrared image and five more holographic infrared images (corresponding to five new voxels) may be captured to be compared to the refreshed base holographic infrared image. The base holographic infrared image may need to be refreshed after a certain amount of time passes due to the movement of tissue over time, for example. In some implementations, a refreshed base holographic infrared image is captured immediately before or immediately after each holographic infrared image is captured.

Process 700 may also include generating a composite image (e.g. 569) of the tissue based on differences between the plurality of holographic infrared images and the base holographic infrared image. In some embodiments, process 700 further includes (1) generating first intensity data corresponding to a first voxel in the plurality of voxels that the ultrasonic signal was directed to while a first holographic infrared image was captured; (2) generating second intensity data corresponding to a second voxel in the plurality of voxels that the ultrasonic signal was directed to while a second holographic infrared image was captured; (3) incorporating the first intensity data as a first voxel value in the composite image; and (4) incorporating the second intensity data as a second voxel value in the composite image.

Figure 8:
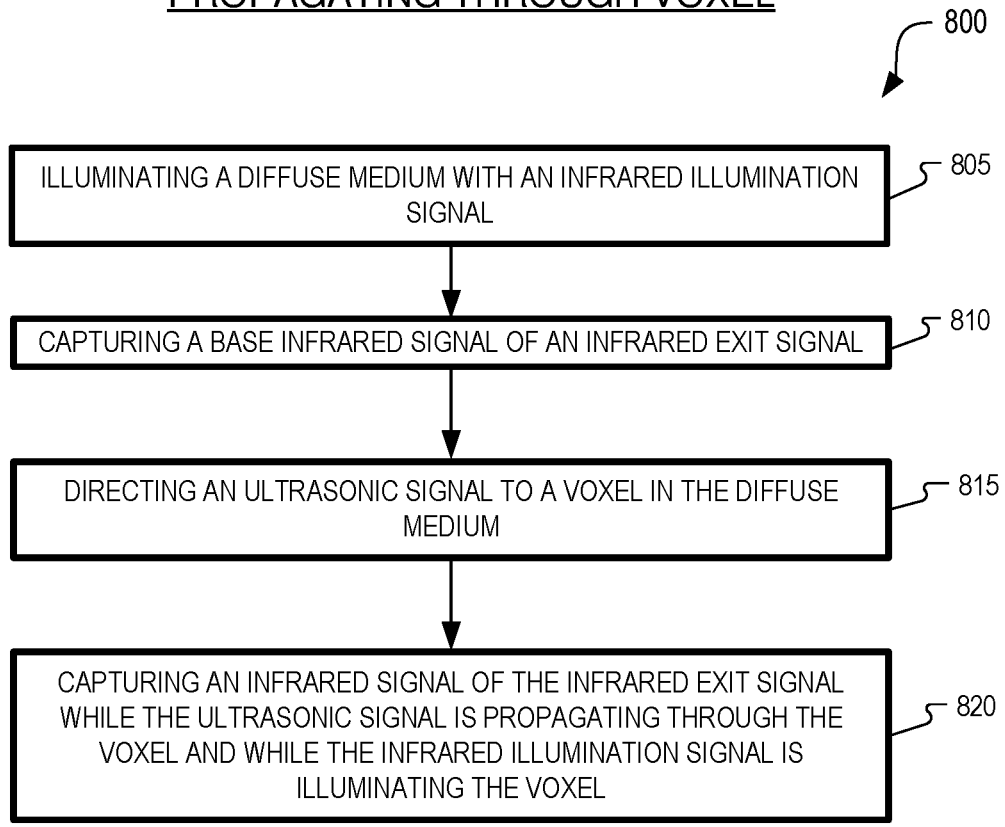
FIG. 8 illustrates an example flow chart of a process of capturing an infrared signal of an infrared exit signal while an ultrasonic signal is propagating through a voxel, in accordance with an embodiment of the disclosure.

FIG. 8 illustrates an example flow chart of a process 800 of capturing an infrared signal of an infrared exit signal while an ultrasonic signal is propagating through a voxel, in accordance with an embodiment of the disclosure. The order in which some or all of the process blocks appear in process 800 should not be deemed limiting. Rather, one of ordinary skill in the art having the benefit of the present disclosure will understand that some of the process blocks may be executed in a variety of orders not illustrated, or even in parallel. Processing logic 101, 201, or 401 may execute some or all of the operations of process 800, for example.

In process block 805, a diffuse medium is illuminated with an infrared illumination signal. The infrared illumination signal may be near-infrared light. The diffuse medium may include tissue.

In process block 810, a base infrared signal of an infrared exit signal is captured. The infrared exit signal is the infrared illumination signal exiting the diffuse medium.

In process block 815, an ultrasonic signal is directed to a voxel in the diffuse medium.

In process block 820, an infrared signal of the infrared exit signal is captured while the ultrasonic signal is propagating through the voxel and while the infrared illumination signal is illuminating the voxel.

Process 800 may also include generating a composite image (e.g. 569) of the diffuse medium based on a difference between the infrared signal and the base infrared signal.

In an embodiment of process 800, the base infrared signal captures an interference of the infrared exit signal and an infrared reference beam having a same wavelength as the infrared exit signal. The base infrared signal is captured while the ultrasonic signal is not propagating through the diffuse medium and the infrared signal captures a second interference of the infrared exit signal and the infrared reference beam while the ultrasonic signal is propagating through the voxel. A same laser source may be optically coupled to generate the infrared illumination signal and the infrared reference beam.

The processes explained above are described in terms of computer software and hardware. The techniques described may constitute machine-executable instructions embodied within a tangible or non-transitory machine (e.g., computer) readable storage medium, that when executed by a machine will cause the machine to perform the operations described. Additionally, the processes may be embodied within hardware, such as an application specific integrated circuit ("ASIC") or otherwise.

A tangible non-transitory machine-readable storage medium includes any mechanism that provides (i.e., stores) information in a form accessible by a machine (e.g., a computer, network device, personal digital assistant, manufacturing tool, any device with a set of one or more processors, etc.). For example, a machine-readable storage medium includes recordable/non-recordable media (e.g., read only memory (ROM), random access memory (RAM), magnetic disk storage media, optical storage media, flash memory devices, etc.).

Communication channels described in this disclosure may include wired or wireless communications utilizing IEEE 802.11 protocols, BlueTooth, SPI (Serial Peripheral Interface), I²C (Inter-Integrated Circuit), USB (Universal Serial Port), CAN (Controller Area Network), cellular data protocols (e.g. 3G, 4G, LTE, 5G), or otherwise The above description of illustrated embodiments of the invention, including what is described in the Abstract, is not intended to be exhaustive or to limit the invention to the precise forms disclosed. While specific embodiments of, and examples for, the invention are described herein for illustrative purposes, various modifications are possible within the scope of the invention, as those skilled in the relevant art will recognize.

These modifications can be made to the invention in light of the above detailed description. The terms used in the following claims should not be construed to limit the invention to the specific embodiments disclosed in the specification. Rather, the scope of the invention is to be determined entirely by the following claims, which are to be construed in accordance with established doctrines of claim interpretation.

What is claimed is:

1. A method of medical imaging comprising:
   illuminating tissue with an infrared illumination signal having an infrared wavelength;
   interfering an infrared reference beam with an infrared exit signal, wherein the infrared exit signal is the infrared illumination signal exiting the tissue, and wherein the infrared reference beam has the infrared wavelength that is the same as the infrared illumination signal;
   capturing a base holographic infrared image of an interference of the infrared reference beam with a base infrared exit signal;
   scanning an ultrasound emitter to direct an ultrasonic signal to a plurality of voxels of the tissue while the infrared illumination signal is illuminating the tissue, wherein the base holographic infrared image is captured when the ultrasonic signal is not propagating through the tissue; and
   capturing a plurality of holographic infrared images corresponding to the plurality of voxels that the ultrasound emitter is scanned to, the plurality of holographic images capturing an interference of the infrared reference beam with the infrared exit signal at a time when the ultrasonic signal is directed to a particular voxel in the plurality of voxels.

2. The method of claim 1 further comprising:
generating a composite image of the tissue based on differences between the plurality of holographic infrared images and the base holographic infrared image.

3. The method of claim 2, wherein generating the composite image includes:
generating first intensity data corresponding to a first voxel in the plurality of voxels that the ultrasonic signal was directed to while a first holographic infrared image was captured;
generating second intensity data corresponding to a second voxel in the plurality of voxels that the ultrasonic signal was directed to while a second holographic infrared image was captured;
incorporating the first intensity data as a first voxel value in the composite image; and
incorporating the second intensity data as a second voxel value in the composite image.

4. A method comprising:
activating an ultrasound emitter to launch an ultrasonic signal into a diffuse medium;
illuminating the diffuse medium with an infrared illumination signal having an infrared wavelength;
interfering an infrared reference beam with an infrared exit signal, wherein the infrared exit signal is the infrared illumination signal exiting the diffuse medium, and wherein the infrared reference beam has the infrared wavelength that is the same as the infrared illumination signal;
capturing an infrared image of the interference of the infrared reference beam with the infrared exit signal;
generating first intensity data from the infrared image, wherein the ultrasonic signal is focused to a first voxel while the infrared image is being captured; and
incorporating the first intensity data as a first voxel value in a composite image of the diffuse medium, the first voxel value corresponding to a first voxel position in the composite image.

5. The method of claim 4, wherein the infrared image is captured while the ultrasonic signal is propagating through the diffuse medium.

6. The method of claim 5 further comprising:
illuminating the diffuse medium with a base infrared illumination signal having the infrared wavelength that is the same as the infrared reference beam, the base infrared illumination signal illuminating the diffuse medium at a time different than when the infrared illumination signal illuminates the diffuse medium; and
capturing a base infrared image while the ultrasonic signal is not propagating through the diffuse medium and while the based infrared illumination signal is propagating through the diffuse medium, the base infrared image capturing an interference of the infrared reference beam with a base infrared exit signal that is the base infrared illumination signal exiting the diffuse medium.

7. The method of claim 4, wherein the infrared illumination signal is near-infrared light.

8. The method of claim 4, wherein the diffuse medium includes tissue.

9. The method of claim 4, wherein capturing the infrared image include capturing the infrared image with an image sensor.

10. The method of claim 4, wherein a same laser source is optically coupled to generate the infrared illumination signal and the infrared reference beam.

11. The method of claim 4, wherein the ultrasound emitter is configured to be directed to different voxels in the diffuse medium.

12. The method of claim 4, wherein the infrared image is a holographic infrared image.

13. A method comprising:
illuminating a diffuse medium with an infrared illumination signal;
capturing a base infrared signal of an infrared exit signal, wherein the infrared exit signal is the infrared illumination signal exiting the diffuse medium;
directing an ultrasonic signal to a voxel in the diffuse medium; and
capturing an infrared signal of the infrared exit signal while the ultrasonic signal is propagating through the voxel and while the infrared illumination signal is illuminating the voxel,
wherein the base infrared signal captures an interference of the infrared exit signal and an infrared reference beam having a same wavelength as the exit signal, the base infrared signal captured while the ultrasonic signal is not propagating through the diffuse medium,
and wherein, the infrared signal captures a second interference of the infrared exit signal and the infrared reference beam while the ultrasonic signal is propagating through the voxel.

14. The method of claim 13 further comprising:
generating a composite image of the diffuse medium based on a difference between the infrared signal and the base infrared signal.

15. The method of claim 13, wherein a same laser source is optically coupled to generate the infrared illumination signal and the infrared reference beam.

16. The method of claim 13, wherein the infrared illumination signal is near-infrared light.

17. The method of claim 13, wherein the diffuse medium includes tissue.

* * * * *